United States Patent
Worrell et al.

(10) Patent No.: US 12,364,590 B2
(45) Date of Patent: Jul. 22, 2025

(54) DEVICES FOR PROVIDING TISSUE SUPPORT DURING BREAST RECONSTRUCTION, AND SYSTEMS AND METHODS THEREOF

(71) Applicant: Melodi Health, Inc., Minneapolis, MN (US)

(72) Inventors: Sarah M. Worrell, Hopkins, MN (US); Hunter R. Moyer, Rapid City, SD (US); Kaitlyn M. Roth, Minneapolis, MN (US); Eric J. Krause, Big Lake, MN (US); Daniel Johnson, Minneapolis, MN (US); John K. Swain, St. Paul, MN (US); Dane D. Hart, Minneapolis, MN (US)

(73) Assignee: Melodi Health, Inc., Minneapolis, MN (US)

( * ) Notice: Subject to any disclaimer, the term of this patent is extended or adjusted under 35 U.S.C. 154(b) by 0 days.

(21) Appl. No.: 18/886,843

(22) Filed: Sep. 16, 2024

(65) Prior Publication Data
US 2025/0134646 A1    May 1, 2025

Related U.S. Application Data

(60) Provisional application No. 63/546,124, filed on Oct. 27, 2023.

(51) Int. Cl.
*A61F 2/12* (2006.01)

(52) U.S. Cl.
CPC ............. *A61F 2/12* (2013.01); *A61L 2430/04* (2013.01)

(58) Field of Classification Search
CPC ................................ A61F 2/12; A61L 2430/04
See application file for complete search history.

(56) References Cited

U.S. PATENT DOCUMENTS 6,652,595 B1 * 11/2003 Nicolo .................. A61F 2/0063
                                                       623/23.72
8,315,700 B2    11/2012 Citron et al.
(Continued)

FOREIGN PATENT DOCUMENTS

| WO | WO-2007050382 A1 | 5/2007 |
| WO | WO-2014149096 A1 | 9/2014 |
| WO | WO-2021108162 A1 | 6/2021 |

OTHER PUBLICATIONS

Chun et al., "Implant-Based Breast Reconstruction Using Acellular Dermal Matrix and the Risk of Postoperative Complications", Feb. 2010, 8 pages.

(Continued)

*Primary Examiner* — Suzette J Gherbi
(74) *Attorney, Agent, or Firm* — COOLEY LLP

(57) ABSTRACT

Embodiments described herein relate to a support device configured to provide tissue support, during implant-based breast surgery. Embodiments described herein include a matrix sheet disposed in a foldable sheet including one or more templates including at least one of a partial support template and a full support template. The partial support template is configured for use in shaping the matrix sheet into a support device for partial coverage for a breast prosthesis. The full support template is configured for use in shaping the matrix sheet into a support device for full coverage for a breast prosthesis. In some embodiments, the support device is a bioabsorbable mesh substrate, a bioabsorbable polymer coating, and one or more active pharmaceutical agents for delivery at the surgical site. The support device may be provided in various shapes for coverage of the breast prosthesis or provided with templates for various coverage of the breast prosthesis. The support device forms (Continued)

a macroporous scaffold, and the macroporous scaffold may act as a lattice for new tissue ingrowth.

39 Claims, 15 Drawing Sheets

(56) References Cited

U.S. PATENT DOCUMENTS

| | | | |
|---|---|---|---|
| 8,591,531 B2 | 11/2013 | Buevich et al. | |
| 8,636,753 B2 | 1/2014 | Buevich et al. | |
| 8,858,629 B2 | 10/2014 | Moses et al. | |
| 9,233,192 B2 | 1/2016 | Schwartz et al. | |
| 9,457,129 B2 | 10/2016 | Buevich et al. | |
| 9,848,955 B2 | 12/2017 | Buevich et al. | |
| 9,987,116 B2 | 6/2018 | Buevich et al. | |
| 10,058,417 B2 | 8/2018 | Limem et al. | |
| 10,307,237 B2 | 6/2019 | Wang et al. | |
| 10,363,127 B2 | 7/2019 | Mlodinow et al. | |
| 10,420,864 B2 | 9/2019 | Pulapura et al. | |
| 10,813,743 B2 | 10/2020 | Spiegel et al. | |
| 10,945,831 B2 | 3/2021 | Bunce et al. | |
| 2007/0123915 A1* | 5/2007 | Kammerer | A61F 2/0095 606/151 |
| 2009/0149953 A1* | 6/2009 | Schuessler | A61F 2/12 623/8 |
| 2009/0240342 A1* | 9/2009 | Lindh, Sr. | B29C 43/003 425/161 |
| 2010/0124563 A1* | 5/2010 | Coleman | A61L 27/56 435/307.1 |
| 2011/0035004 A1* | 2/2011 | Maxwell | A61L 27/362 623/8 |
| 2011/0257761 A1* | 10/2011 | Mortarino | D04B 1/22 623/23.72 |
| 2011/0301706 A1* | 12/2011 | Brooks | A61F 2/12 623/8 |
| 2012/0283826 A1* | 11/2012 | Moses | A61L 31/146 623/8 |
| 2013/0018393 A1* | 1/2013 | Bengtson | A61B 17/0644 606/139 |
| 2013/0211519 A1* | 8/2013 | Dempsey | A61B 90/39 623/8 |
| 2013/0253645 A1* | 9/2013 | Kerr | A61F 2/12 623/8 |
| 2014/0081397 A1* | 3/2014 | Kalus | A61F 2/12 623/8 |
| 2021/0260245 A1 | 8/2021 | Peres et al. | |
| 2022/0053755 A1 | 2/2022 | Merboth et al. | |
| 2023/0158557 A1* | 5/2023 | Connell | A61B 7/02 600/586 |

OTHER PUBLICATIONS

Delong et al., "Review of Outcomes in Prepectoral Prosthetic Breast Reconstruction With and Without Surgical Mesh Assistance", Feb. 2021, 11 pages.

Louw et al., "Prepectoral Breast Reconstruction", Nov. 2017, 9 pages.

Phillips et al., "A Systematic Review of Infection Rates and Associated Antibiotic Duration in Acellular Dermal Matrix Breast Reconstruction", Nov. 11, 2014, 14 pages.

Tasoulis et al., "Subcutaneous Implant Breast Reconstruction: Time to Reconsider?" 2017, 11 pages.

Viola et al., "Breast Tissue Expander-Related Infections: Perioperative Antimicrobial Therapy", Jan. 2014, 7 pages.

Walia et al., "Prepectoral versus Subpectoral Tissue Expander Placement: A Clinical and Quality of Life Outcomes Study", Apr. 2018, 6 pages.

Invitation to Pay Additional fees for International Application No. PCT/US2024/053077, mailed Jan. 27, 2025, 12 pages.

International Search Report and Written Opinion for PCT Application No. PCT/US2024/053077 mailed Mar. 20, 2025, 19 pages.

* cited by examiner

Partial Coverage

Full Coverage

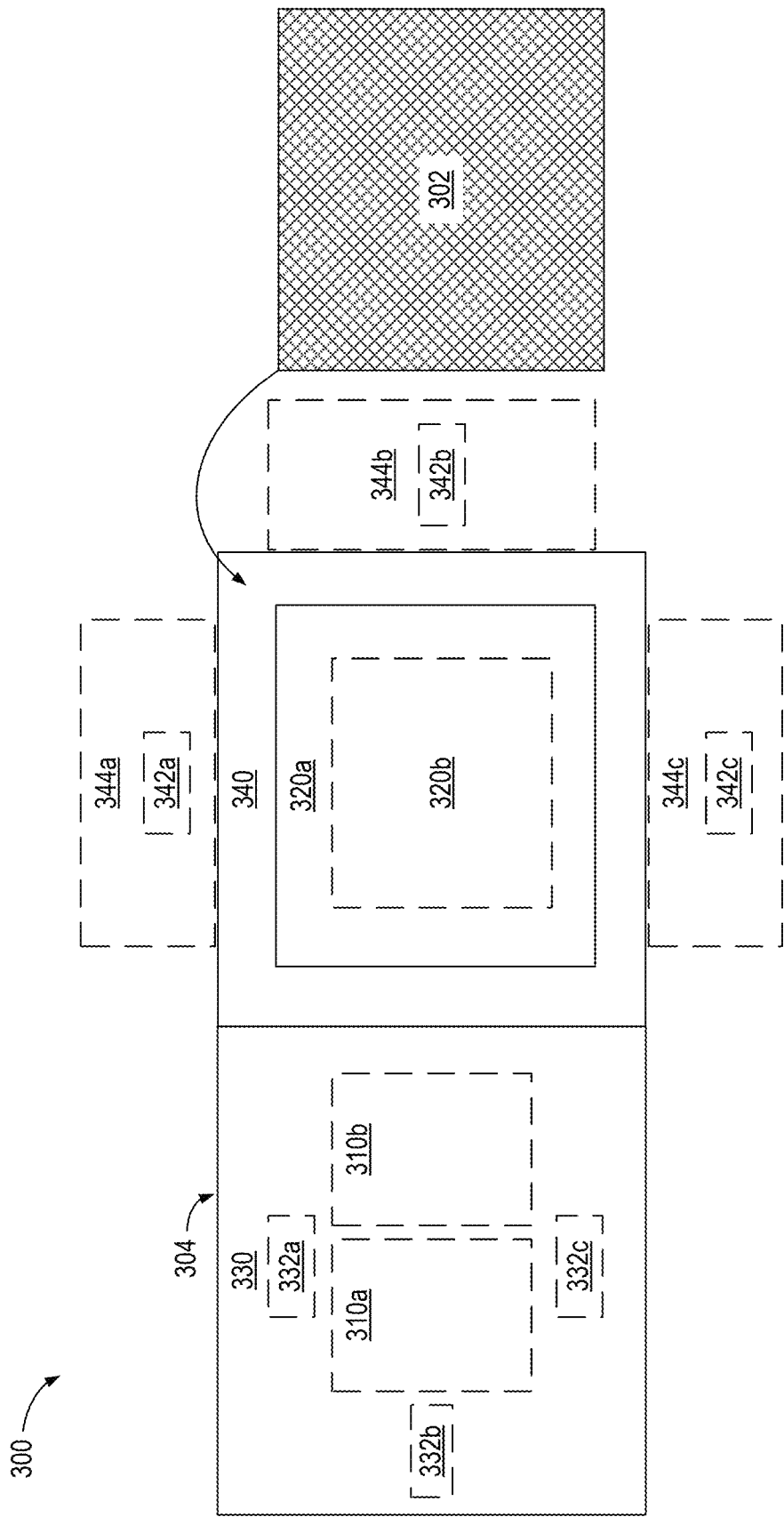

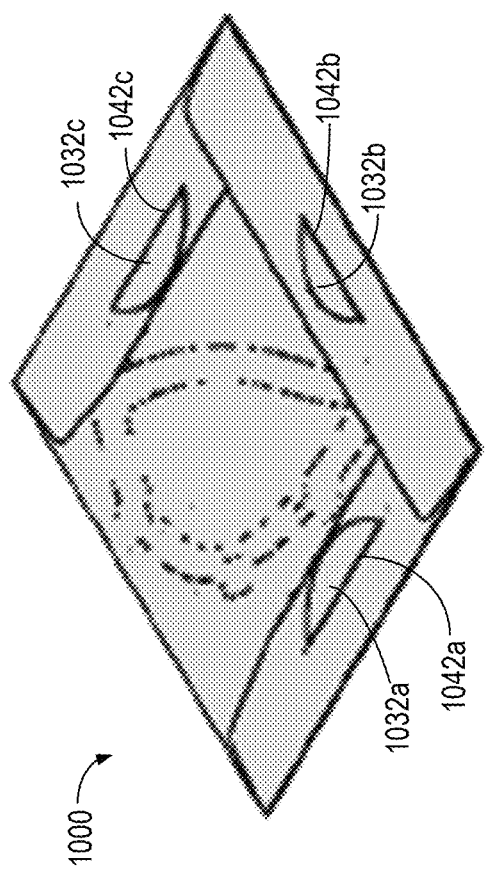

DEVICES FOR PROVIDING TISSUE SUPPORT DURING BREAST RECONSTRUCTION, AND SYSTEMS AND METHODS THEREOF

CROSS-REFERENCING TO RELATED APPLICATIONS

This application claims priority to U.S. Provisional Patent Application No. 63/546,124, filed Oct. 27, 2023, and titled "DEVICES FOR PROVIDING TISSUE SUPPORT DURING BREAST RECONSTRUCTION, AND SYSTEMS AND METHODS THEREOF," the disclosure of which is incorporated herein by reference.

TECHNICAL FIELD

Embodiments described herein relate to devices and methods for providing tissue support during a breast surgery. Specifically, the embodiments described herein relate to a device configured to provide support for a breast prosthesis used in a breast surgery.

BACKGROUND

During breast augmentation and/or breast reconstruction procedures, breast implants (e.g., tissue expander and/or permanent breast implant) may be placed above or beneath the chest muscle (pectoralis major). Support device technologies (e.g., acellular dermal matrices (ADM) and surgical mesh) can be used in such procedures. However, current support device technologies (e.g., ADM and surgical mesh) may contribute to risk of infection in implant-based breast reconstruction.

BRIEF DESCRIPTION OF THE DRAWINGS

FIG. 3A schematically depicts a holder configured to hold or enclose a matrix sheet, which can be shaped into a support device for supporting a breast prosthesis, according to embodiments.

FIG. 10C depicts the holder of FIG. 10A in a closed or folded configuration, where a matrix sheet can be disposed therein.

SUMMARY OF INVENTION

Figure 1A:
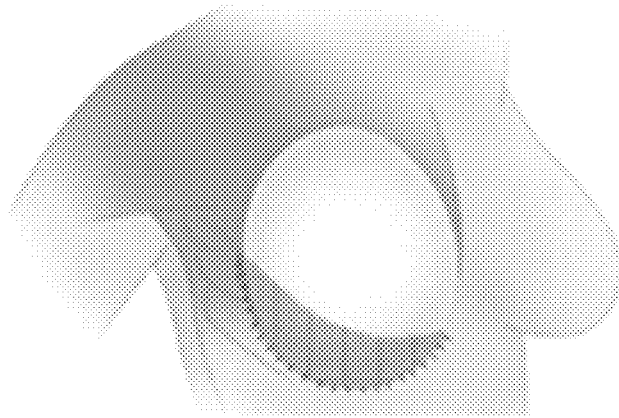
FIG. 1A depicts a partial coverage of a breast prosthesis for breast surgery, according to embodiments.

In some embodiments, a kit includes a matrix sheet and a foldable sheet including one or more templates, the one or more templates including at least one of: a partial support template configured for use in shaping the matrix sheet into a first support device configured to provide partial coverage for a breast prosthesis including a tissue expander or a breast implant; and a full support template configured for use in shaping the matrix sheet into a second support device configured to provide full coverage for a breast prosthesis. The foldable sheet may be configured to be folded into an envelope form that is configured to enclose around the matrix sheet to maintain the matrix sheet in a sterile environment therein.

In some embodiments, an apparatus, includes a body formed of a matrix material, the body configured to be positioned around a breast prosthesis to support a breast prosthesis within a patient. In some embodiments, the body shape may include a central region configured to cover a central portion of an anterior side of a breast prosthesis and a plurality of extensions extending from the central region, each of the plurality of extensions including a first section configured to cover a portion of the anterior side of the breast prosthesis; a second section extending from the first section and having a narrower width than the first section, the second section configured to wrap around a side of the breast prosthesis; and a third section extending from the second section and increasing to a greater width than the second section before tapering to an apex, the third section configured to cover at least a portion of a posterior side of the breast prosthesis, the apex of each of the plurality of extensions configured to be coupled to one another at a posterior side of the breast prosthesis to secure the body to the breast prosthesis.

In some embodiments, a method includes removing a template from a matrix holder by breaking a set of perforations in the matrix holder that define the template, the matrix holder configured to hold a matrix sheet therein; trimming the matrix sheet to a shape of the template using the template, to produce a support device; positioning the support device to cover at least a portion of a breast prosthesis, the breast prosthesis including a tissue expander or a breast implant; positioning the breast prosthesis and the support device in a patient; and securing the breast prosthesis and the support device within the patient by suturing one or more portions of the support device to at least one of the breast prosthesis or surrounding tissue of the patient.

DETAILED DESCRIPTION OF THE DRAWINGS

Overview

Implant-based breast surgical procedures include breast augmentation to increase the breast size and breast reconstruction to recreate breasts after a mastectomy. During implant-based breast reconstruction, the procedure may be done in a single stage, direct-to-implant, or two-stage. In direct-to-implant based breast reconstruction is a single procedure placing the permanent implant at the time of the mastectomy. In two-stage implant-based breast reconstruction, a tissue expander is placed into the subcutaneous or submuscular breast pocket to stretch the muscle and tissue during the first stage to create space for a permanent breast implant. During the second stage, the tissue expander is removed and replaced with a permanent breast implant. Local complications, such as infection, capsular contracture, seroma, hematoma, and malposition of the implant are a common occurrence in implant-based breast reconstruction surgery and occur at a lower rate in breast augmentation surgery. Use of support devices (e.g., acellular dermal matrices (ADM) and surgical mesh) has been reported to have benefits in implant-based breast reconstruction by supporting soft tissue surrounding the breast prosthesis, limiting breast prosthesis movement, reduction in seroma rates, and reduction of capsular contracture (DeLong M D, et al., "Review of Outcomes in Prepectoral Prosthetic Breast Reconstruction With and Without Surgical Mesh Assistance", February, 2021), (Tasoulis M K, et al., "Subcutaneous Implant Breast Reconstruction: Time to Reconsider?" September, 2017), Walia G S, et al., "Pre-pectoral versus Sub-Pectoral Tissue Expander Placement: A Clinical and Quality of Life Outcomes Study", April, 2018), (Ter Louw R P, M Y Nahabedian, "Prepectoral Breast Reconstruction", November 2017). However, risk of infection, often requiring explanation, has been identified as a concern in implant-based breast reconstruction, and use of current support device technologies (e.g., ADM and surgical mesh) may contribute to this risk (Chun Y S, et al., "Implant-Based Breast Reconstruction Using Acellular Dermal Matrix and the Risk of Postoperative Complications," February, 2010), (Viola G, R. I., "Breast tissue expander related infections: Perioperative antimicrobial therapy," January, 2014), (Phillips B T, et al., "A Systematic Review of Infection Rates and Associated Antibiotic Duration in Acellular Dermal Matrix Breast Reconstruction," February, 2014). The literature also reports the microorganisms *Staphylococcus epidermidis* (with and without methicillin resistance), *Staphylococcus aureus* (with and without methicillin resistance), and *Pseudomonas aeruginosa* are most frequently Present in breast implant infections, in addition to *Klebsiella pneumonia, Acinetobacter baumannii* and *Escherichia coli*.

Device Description

2.1 Systems and Devices

Embodiments described herein relate to a support device for a breast prosthesis for breast surgery. The breast prosthesis may include a tissue expander or a breast implant. The support device is formed from a matrix and is configured to be implanted into a patient to provide tissue support during breast surgery. In some embodiments, the support device can be used to provide soft tissue support in an implant-based breast reconstruction procedure (e.g., a two stage post-mastectomy alloplastic prepectoral breast reconstruction procedure) or in a breast augmentation procedure. In some embodiments, the support device may provide benefits including reinforcement of soft tissue, stabilization of the breast prosthesis while native soft tissue heals, and decreased risk of infection, biofilm formation, capsular contracture, seroma, hematoma, and/or malposition.

FIG. 1A depicts a partial coverage support device of a breast prosthesis for breast surgery, according to an embodiment. As shown, a support device and breast prosthesis may be positioned in a chest of a patient such that a bottom edge or pole of the breast prosthesis aligns with a bottom edge of the support device. In some embodiments, the support device may be secured or fixed to nearby tissue in a breast pocket of the patient to provide support for the breast prosthesis. For example, a portion of the support device (e.g., a bottom portion) may be secured to nearby tissue such that the support device forms a pocket or sling structure in which the breast prosthesis may be disposed. In this way, the support device may prevent the breast prosthesis from migrating downward and/or pulling on soft tissue in the breast pocket after implantation and while native soft tissue heals.

Figure 1B:
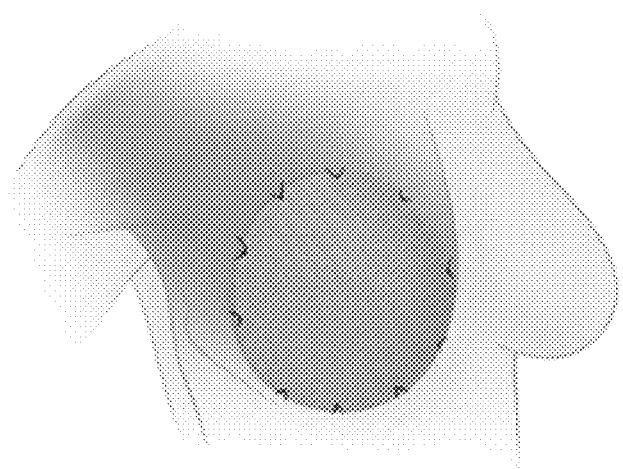
FIG. 1B depicts a full coverage of a breast prosthesis for breast surgery, according to embodiments.

FIG. 1B depicts a full coverage support device of a breast prosthesis for breast surgery, according to embodiments. As shown in FIG. 1B, the support device and/or the breast prosthesis may be positioned such that the support device envelops or covers the breast prosthesis. For example, one or more portions of the support device may wrap around the breast prosthesis, and at least a portion of the support device and/or the breast prosthesis may be secured or fixed to surrounding tissue in the breast pocket of the patient. As shown, a perimeter of the support device may be fixed (e.g., sutured) to surrounding tissue in the breast pocket to secure the breast prosthesis in place after implantation.

Figure 2A:
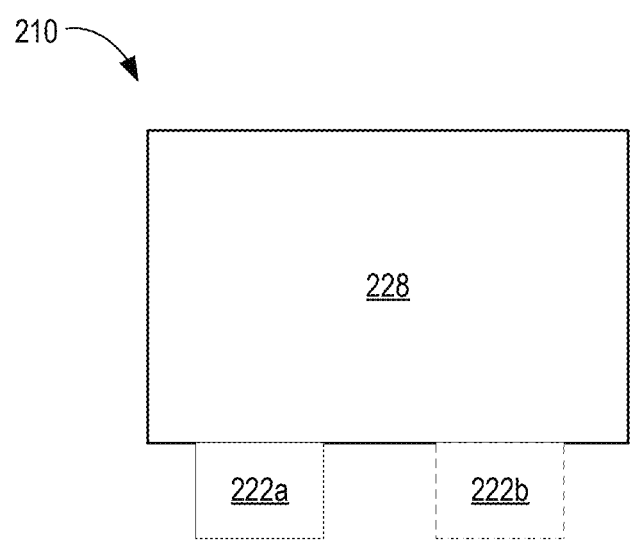
FIG. 2A schematically depicts a template for shaping a support device for supporting a breast prosthesis, according to embodiments.

FIG. 2A schematically depicts a template 210 for shaping a support device for supporting a breast prosthesis, according to an embodiment. The template 210 may include a central region 228 and one or more extensions (e.g., tabs, flaps, tags, etc.) 222a, 222b. In some embodiments, extension 222b may be optional. The template 210 may be used to guide trimming (e.g., cutting, tearing, stamping out, etc.) of a matrix sheet (hereinafter, "the matrix") in order to create the support device. A surgeon may use the template 210 to shape the matrix into a desired shape to create the support device; therefore, the shape of the template 210 may correspond to the desired shape of the support device. A shape of the central region 228 of the template may correspond to a shape of a central region of the support device. The central region of the support device may be configured to wrap around a portion (e.g. a bottom portion) of the breast prosthesis. In some embodiments, the central region 228 of the template, and therefore a central region of the support device, may have any suitable shape including, but not limited to, a crescent, a circle, a semi-circle, an oval/ellipse, a semi-oval/ellipse, a square, a rectangle, a trapezoid, etc. In some embodiments, the central region 228 may include an irregular shape having a wide center portion and tapering to points on each end. In some embodiments, the central region 228 of the template 220 and the central region of the support device may have dimensions corresponding to the breast prosthesis.

For example, the central region of the support device may include a rounded shape having an average curvature and/or an average radius corresponding to a curvature and/or radius of the breast prosthesis such that a curved portion of the central region of the support device may align with a portion of a perimeter of the breast prosthesis. Therefore, when the support device is secured to surrounding tissue, the breast prosthesis may fit in an opening defined by the central region of the support device and native tissue. In some embodiments, the central region 228 may be an ellipse or crescent shape having a major axis (e.g., a width of the shape) and a minor axis (e.g., 2× a length of the shape). The dimensions of the central region 228 of the template are described in further detail with respect to FIGS. 5 and 6.

Additionally, the one or more extensions 222a, 222b of the template may correspond to one or more extensions of the support device. The extensions of the support device may be configured to secure the support device to tissue in the chest of the patient. For example, the extensions of the support device may be affixed to tissue near the breast prosthesis (e.g., via sutures) to hold the support device and the breast prosthesis in place. In some embodiments, the template 210, and therefore the support device, may include any suitable number of extensions such that the support device can be secured to itself or to surrounding tissue in the chest of the patient when implanted. In some embodiments, the template 210, and therefore the support device, may include 1 extension to 20 extensions, inclusive of all ranges and subranges therebetween. In some embodiments, the support device may include 1 extension to 12 extensions, inclusive of all ranges and subranges therebetween. In some embodiments, the template 210, and therefore the support device, may include 2 extensions 222a, 222b. In some embodiments the template 210, and therefore the support device, may include 3 extensions 222. In some embodiments, the extensions 222 may be distributed along a portion of the central region 228. For example, the extensions 222 may be distributed along a bottom edge of the central region 228 such that the bottom edge of the support device may be sutured to tissue underneath a location at which the breast prosthesis is implanted. The extensions 222a, 222b of the template, and therefore the extensions of the support device, may have any suitable shape with or without rounded edges including, but not limited to, a square, a rectangle, a trapezoid, a circle, an oval/ellipse, a semi-circle or semi-oval/ellipse. In some embodiments, the extensions 222a, 222b may have a maximum width that may be between about 10% the width of the center region 228 to about 90% the width of the center region 228, inclusive of all ranges and subranges therebetween. In some embodiments, the maximum width of the extensions 222a, 222b may be between about 66% (or about ⅔) the width of the center region 228 to about 75% (or about ¾) the width of the center region 228, inclusive of all ranges and subranges therebetween. In some embodiments, the extensions 222a, 222b may have a maximum length that may be between about 10% the length of the center region 228 to about 90% the total length of the center region, inclusive of all ranges and subranges therebetween. In some embodiments, the maximum length of the extensions 222a, 222b may be between about 66% (or ⅔) the length of the center region 228 to about 75% (or about ¾) the length of the center region 228. In some embodiments, the maximum width and the maximum length of the extensions 222a, 222b may vary based on a size of the breast prosthesis, a shape of the breast prosthesis, and a location of the extensions 222a, 222b. In some embodiments, the partial support device including the crescent shape may be used for prepectoral implant procedures and/or for submuscular implant procedures.

In some embodiments, a width of the center region 228 may be in a range such that the support device covers a lower half of the anterior surface of various breast implant sizes (e.g., 100 cc-1400 cc) and extends beyond a lower edge of the breast implant for suturing a portion of the support device to tissue adjacent to the lower edge. In some embodiments, a size of the extensions 222a, 222b may correspond to (e.g., be similar to) a size of suture tabs on commercially available tissue expanders. For example, the extensions 222a, 222b may have substantially similar dimensions (e.g., within 5%) as suture tabs on the tissue expander such that the extensions 222a, 222b and the suture tabs can be easily aligned and coupled to one another. In some embodiments, a number of extensions 222a, 222b and a positioning of the extensions 222a, 222b on the support device may correspond to a number and positioning of suture tabs on the tissue expander. For example, the tissue expander may have suture tabs at certain positions along its circumference, and the support device may include an extension positioned to align with one or more suture tabs or to be positioned so the suture tabs are not covered by the matrix.

Figure 2B:
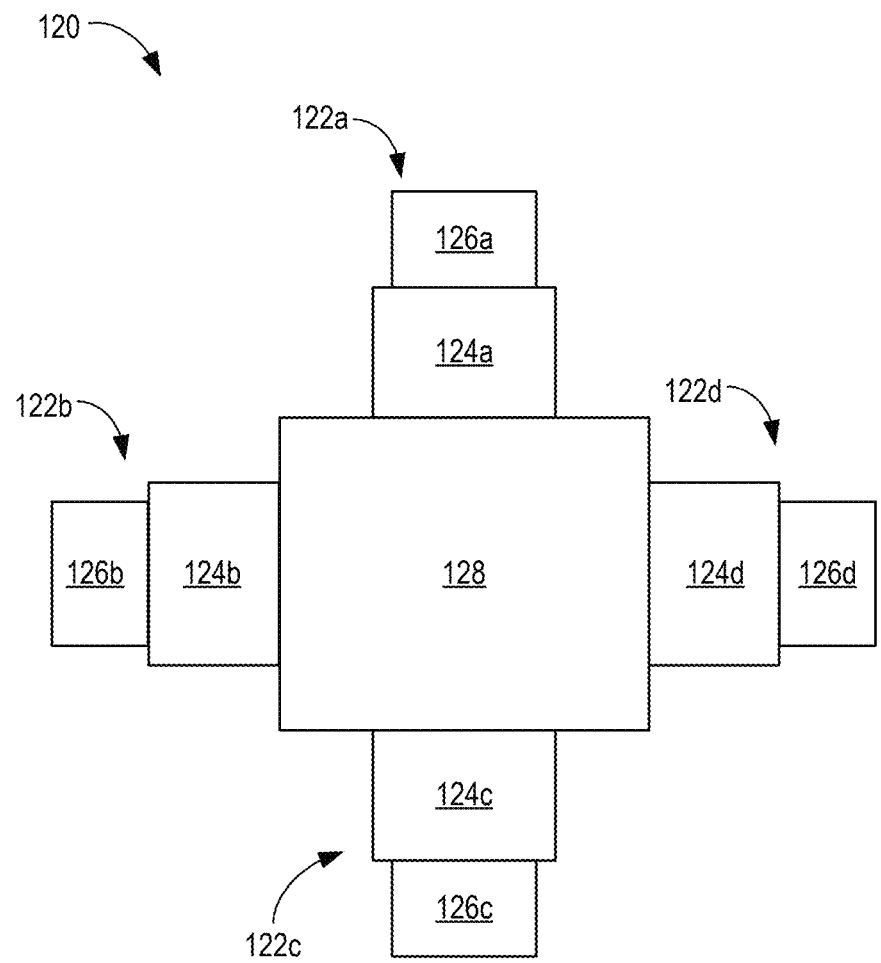
FIG. 2B schematically depicts a template for shaping a support device for supporting a breast prosthesis, according to embodiments.

FIG. 2B schematically depicts a template for shaping a support device for supporting a breast prosthesis, according to embodiments. Some aspects of the template 120 and the support device may be structurally and/or functionally similar to the template 210 and support device described with respect to FIG. 2A; therefore, certain aspects of the template 120 and the support device are not described herein with respect to FIG. 2B. As shown, the template 120 includes a body having a central region 128 and a plurality of extensions (e.g., petals, tabs, portions, etc.) 122a, 122b, 122c, 122d extending from the central region 128. In some embodiments, the plurality of extensions includes a first extension 122a, a second extension 122b, a third extension 122c, and a fourth extension 122d. Each extension 122a-122d may include at least a first section 124a, 124b, 124c, 124d and a second section 126a, 126b, 126c, 126d.

A surgeon may use the template 120 to shape a matrix into a desired shape to create the support device. Therefore, a shape of the template 120 may correspond to a shape of the support device. Specifically, a shape of the central region 128 of the template may correspond to a shape of the central region of the support device. The support device may be configured to be wrapped around a breast prosthesis and implanted with the breast prosthesis within a patient. In some embodiments, the central region of the support device may be configured to cover at least a portion of an anterior side of the breast prosthesis. In some embodiments, a length and a width of the central region 128 of the template, and therefore a length and a width of the support device, may correspond to a length and a width of the breast prosthesis such that the central region of the support device covers all or nearly all of the anterior side of the breast prosthesis. The dimensions of the central region 128 of the template and therefore the central region of a full coverage support device is described in further detail with respect to FIG. 8.

Additionally, the shapes of the first extension 122a, the second extension 122b, the third extension 122c, and the fourth extension 122d of the template may correspond to shapes of the first extension, the second extension, the third extension, and the fourth extension of the support device. While shown with 4 extensions in FIG. 2B, the template 120, and therefore the support device, may include any suitable number and/or location of extensions. In some embodiments, the template 120, and therefore the support device, may include 2 extensions, 3 extensions, 4 extensions, 5 extensions, 6 extensions, 7 extensions, 8 extensions, 9 extensions, 10 extensions, 11 extensions, or 12 extensions. In some embodiments, the template 120, and therefore the support device, may form a shape including, for example, a flower or petal shape, a cross, an "X" shape, a "Y" shape, an asterisk shape, or any suitable shape such that the support device may envelope the breast prosthesis. In some embodiments, full coverage support device may be used for prepectoral breast implant procedures.

In some embodiments, the full coverage support device includes more than 2 extensions such that the support device covers a predetermined surface area (e.g., above 50%, above 60%, above 70%, above 80%, above 90%, above 95%) of the tissue expander. In some embodiments, the full coverage support device includes 4 extensions such that the extensions can cover the predetermined surface area with less suturing and preparation time. In some embodiments, a number of extensions of the full coverage support device may correspond to suture tabs on the tissue expander. For example, the extensions of the full coverage support device may be positioned such that the suture tabs of the tissue expander align with an inner apex between the extensions (e.g., the point between two extensions where the extensions and the central region 128 meet).

A first section of each extension of the support device may be configured to cover a portion of the anterior side of the breast prosthesis and/or a portion of a side of the breast prosthesis. In some embodiments, the second section of the support device may wrap around the side of the breast prosthesis to a posterior side of the breast prosthesis such that each second section of the support device covers a portion of a posterior side of the breast prosthesis. In some embodiments, a width of each extension 122a-122d of the template 120, and therefore a width of each extension of the support device, may vary along a length of the extension. In some embodiments, a maximum width of the second section 126a-126d of the template 120 and support device may be smaller than a maximum width of the first section 124a-124d of the template 120 and support device. For example, the second section 126a-126d of the support device may taper to an apex, and the apex of each of the plurality of extensions of the support device may be configured to be coupled to one another at the posterior side of the breast prosthesis to secure the body of the support device to the breast prosthesis. In some embodiments, the extensions 122a-122d of the template 120, and therefore the extensions of the support device, may have a constant width along a length of each extension 122a-122d. For example, each extension 122a-122d may form a rectangular shape.

Alternatively or additionally, each extension 122a-122d of the template 120, and therefore each extension of the support device, may include a first section, a second section, and a third section extending from the second section. In some embodiments, the second section may function as a transition section, e.g., to provide a transition from the first section to the third section. In some embodiments, the first section and the third section of the template, and therefore the support device, may have a width greater than that of the second section. In some embodiments, the first section and the third section of the template, and therefore the support device, may have a width smaller than that of the second section. In some embodiments, the third section of the template, and therefore the third section of the support device, may increase to a greater width than that of the second section before tapering to an apex. The third section of the support device may be configured to cover at least a portion of a posterior side of the breast prosthesis, and the apex of each of the plurality of extensions of the support device may be configured to be coupled to one another at the posterior side of the breast prosthesis to secure the body of the support device to the breast prosthesis. In some embodiments, a maximum width of the third section of the template 120, and therefore a maximum width of the third section the support device, is smaller than a maximum width of the first section of each of the extensions. In some embodiments, the first section, second section, and third sections of each extension may form continuous curves (e.g., without discontinuities) that extend from the central region and terminate at the apex of each of the plurality of extensions. While first, second, and third sections are used to describe the extensions herein, it can be appreciated that these can be viewed as a single section with the features of the first, second, and third section (as described above), or fewer or additional sections with such features. Further details regarding the extensions including the first section, the second section, and the third section are described with respect to FIG. 8.

In some embodiments, the support device may be configured to be affixed to the surrounding tissue via sutures along a perimeter of the support device, as shown in FIG. 1B. In some embodiments, the template 120, and therefore the support device, may optionally include a second set of extensions configured to be distributed along a perimeter of the support device when the support device is wrapped around the breast prosthesis. Alternatively or additionally, the breast prosthesis may include a set of extensions (e.g., tabs, tags, portions, etc.) along a perimeter of the breast prosthesis and configured to be affixed (e.g., via suture) to nearby tissue in the chest of the patient. In some embodiments, the support device may be configured to be affixed to itself on a posterior side of the breast prosthesis. For example, the extensions 122a-122d may be wrapped around the breast prosthesis and the apex of each of the third sections 126a-126d may be affixed to one another.

FIG. 3A schematically depicts a matrix holder 300 configured to hold or enclose a matrix 302, which can be shaped into a support device for supporting a breast prosthesis, according to embodiments. In some embodiments, the matrix holder 300 may include a foldable sheet 304 configured to be folded into an envelope that is configured to enclose around the matrix 302. The foldable sheet 304 may include a first section 330 that can be folded over a second section 340 to form the envelope. The foldable sheet 304 may include or define one or more templates 310a, 310b, 320a, 320b. For example, the foldable sheet 304 may include one or more sets of perforations, each set of perforations defining at least one template. In some embodiments, the perforations may be configured such that a user (e.g., the surgeon) may easily separate (e.g., cut out, tear, or punch out) the template shape 310a, 310b, 320a, 320b from the foldable sheet 304. In some embodiments, the foldable sheet 304 may include one or more sets of printed lines defining at least one template. The printed lines may be configured such that a user (e.g., the surgeon) may trace the template on the device or cut out the template shape 310a, 310b, 320a, 320b from the foldable sheet 304. In some embodiments, the templates 310a, 310b, 320a, 320b may each have different shapes and/or sizes to accommodate different procedures and/or patient anatomies. In some embodiments, the templates 310a, 310b, 320a, 320b may have any suitable arrangement on the foldable sheet 304. In some embodiments, one or more templates 310a, 310b, 320a, 320b may be separate from the foldable sheet 304. For example, the matrix holder 300 may be configured to receive one or more pre-shaped or pre-cut templates 310a, 310b, 320a, 320b and the matrix sheet 302 therein. In some embodiments, one or more sheets separate from the foldable sheet 304 may be disposed in the foldable sheet 304 and may include perforations or printed lines defining the one or more templates 310a, 310b, 320a, 320b. In some embodiments, the one or more templates 310a, 310b, 320a, 320b may be pre-shaped and disposed in the foldable sheet 304 with the matrix sheet 302.

As shown in FIG. 3A, the first section 330 of the foldable sheet 304 may include a first template 310a or, optionally, a first set of templates 310a, 310b. Optionally, the second section 340 may include a second template 320a or a second set of templates 320a, 320b. In some embodiments, the foldable sheet 304 may include at least one partial support template (e.g., a first partial support template) 310a configured for use in shaping the matrix into a first support device configured to provide partial coverage for the breast prosthesis. In some embodiments, the foldable sheet 304 may include at least one full support template (e.g., a first full support template) 320a configured for use in shaping the matrix into a second support device configured to provide full coverage for the breast prosthesis. In some embodiments, the first section 330 of the foldable sheet 304 may include the partial support template 310a, and the second section 340 of the foldable sheet 304 may include the full support template. In some embodiments, the foldable sheet 304 may only include one full support template 320a.

In some embodiments the first section 330 may include the first partial support template 310a and a second partial support templates 310b, and the second section 340 may include the full support template 320a. In some embodiments, the first partial support template 310a may have a first size, and the second partial support template 310b may have a second size different than the first size. In some embodiments, the second size may be smaller than the first size. In some embodiments, the first partial support template 310a and the second partial support template 310b may be adjacent to one another on the first section 330. In some embodiments, the first partial support template 310a may include the second partial support template 310b, a border surrounding the second partial support template 310b, and a set of perforations disposed between the border and the second partial support template, the first partial support template being convertible into the second partial support template by separating (e.g., breaking, cutting or tearing) along the perforation to remove the border. For example, perforations corresponding to the second partial support template 310b may be positioned within an area defined by the perforations corresponding to the first partial support template 310a. In some embodiments, the foldable sheet 304 may include a second full support template 320b. The partial support template(s) 310a, 310b and the full support template(s) 320a, 320b may be structurally and/or functionally similar to the partial support template(s) 210 and the full support template(s) 120, and therefore details of the templates 310a-310b and 320a-320b are not described in further detail with respect to FIG. 3A.

In some embodiments, the foldable sheet 304 may optionally include at least one opening or slot 342a, 342b, 342c and at least one tab 332a, 332b, 332c configured to fit through a corresponding slot 342a, 342b, 342c to hold the foldable sheet 304 in the envelope form. For example, the second section 340 of the foldable sheet 304 may include the at least one opening or slot 342a, 342b, 342c and the first section 330 of the foldable sheet 304 may include the at least one tab 332a-332c such that when the first section 330 is folded over the second section 340, the tab(s) 332a-332c may be disposed through the corresponding slot(s) 342a-342c. In some embodiments, the second section 340 of the foldable sheet 304 may optionally include or be coupled to one or more extensions (e.g., foldable pieces, tabs, tags, flaps) 344a, 344b, 344c that extend away from the second section 340. In some embodiments, the slot(s) 342a-342c may each be disposed on a respective extension 344a-344c. In some embodiments, when the first section 330 is folded over the second section 340, the one or more extensions 344a-344c may be folded over an outer surface of the first section 330 (e.g., a surface facing away from the second section 340) to help hold the foldable sheet 304 in envelope form.

Figure 3B:
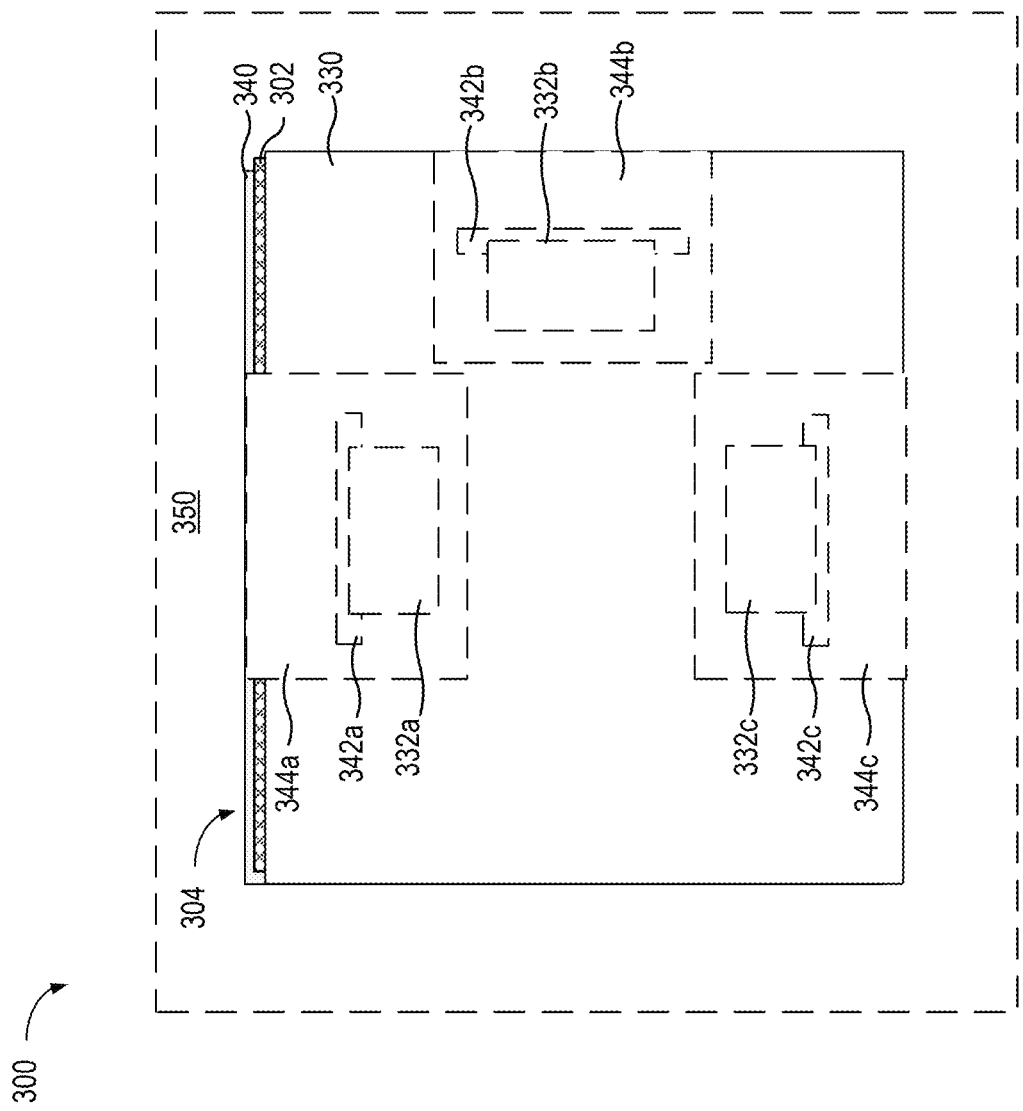
FIG. 3B depicts the holder of FIG. 3A in a closed or folded configuration, where a matrix sheet can be disposed therein.

In some embodiments, a position of the tab(s) 332a-332c on the first section 330 may correspond to a position of the extension(s) 344a-344c and/or slot(s) 342a-342 on the second section 340. For example, when the foldable sheet 304 is folded, the extension(s) 344a-344c may be folded over an outer surface, and the tab(s) 332a-332c may be disposed through the slot(s) 342a-342c, as shown in FIG. 3B. In some embodiments, the holder may include none, one, two, or three extensions, tabs, and/or slots. The extension(s) 344a-344c, tab(s) 332a-332c, and slot(s) 342a-342c may be positioned on an edge of the foldable sheet 304 that is open (e.g., a non-folded edge of the foldable sheet 304). In some embodiments, a first tab 332a may be located near a first edge (e.g., the top edge) of the first section 330, the second tab 332b may be located near a second edge (e.g., an outer side edge) of the first section 330, and the third tab 332c may be located near a third edge (e.g., a bottom edge) of the first section such that when the extension(s) 344a-344c are folded over a portion of the first section 330, one or more open edges of the envelope may be secured closed. The positioning and the dimensions of the extensions 344a-344c, tabs 332a-332c, and slots 342a-342c are described in further detail with respect to FIGS. 10A-10B. Alternatively or additionally, the extension(s) 344a-344c may include adhesive (e.g., tape, gripping material, a gum seal, etc.) such that when the extension(s) 344a-344c are folded from the second section 340 to the first section 330 of the envelope, the extension(s) 344a-344c adhere to the first section 330 to secure the matrix 302 inside the envelope. In some embodiments, any suitable coupled mechanism may be used to close the envelope formed by the foldable sheet 304 including ties, snaps, Velcro®, etc.

In some embodiments, the foldable sheet 304 may include or be formed from a polymer such as, for example, polyethylene, polypropylene, polyethylene terephthalate (PET), nylon, polyacrylonitrile, cellulose, or a combination thereof. In some embodiments, the foldable sheet 304 may include polymer fibers woven into a sheet. In some embodiments, the foldable sheet 304 and/or the templates 310a, 310b, 320a, 320b may include or be formed from Tyvek®, a high-density polyethylene (HDPE). In some embodiments, the foldable sheet 304 may be configured such that the matrix is maintained in a sterile environment when disposed therein. For example, the foldable sheet 304 may be sterilized before the matrix 302 is disposed therein. In some embodiments, the foldable sheet 304 may include an antiseptic to prevent transfer and/or buildup of undesirable contaminants on the matrix 302.

During use, the envelope may be opened (e.g., the tabs 332a-332c may be removed from the slots 342a-342c), the matrix 302 may be removed from inside the envelope, and the templates 310a, 310b, 320a, 320b may be removed (e.g., cut, torn, punched out, etc.) from the foldable sheet 304. Then a template 310a, 310b, 320a, 320b may be used to trim the matrix to accommodate various patient and procedural factors (e.g., breast prosthesis size, desired coverage of the breast prosthesis, and related anatomy). If the surgeon elects to use one of the pre-perforated shape templates, the template 310a, 310b, 320a, 320b is removed from the envelope, placed on the matrix 302, and the matrix 302 is trimmed to the template shape. The templates 310a, 310b, 320a, 320b are configured to accommodate most typical procedures, but surgeons may perform trimming of the matrix 302 to suit the specific dimensional needs of the patient and procedure.

The matrix 302 may be provided in a rectangular shape. In some embodiments, the matrix 302 may be a square or rectangular sheet having a length and/or width between about 25 centimeters (cm) to about 37 cm. In some embodiments, the length of the matrix 302 is about 31 cm and the width is about 26 cm. In some embodiments, the length of the matrix 302 is about 31.2 cm, and the width is about 26.4 cm. In some embodiments, the length of the matrix 302 is about 31.7 cm, and the width is about 26.7 cm. In some embodiments, the area of the matrix 302 is between about 815 cm$^2$ to about 830 cm$^2$. In some embodiments, the area of the matrix 302 is about 823.68 cm$^2$. While shown as a rectangle, the matrix 302 may be provided in any suitable shape such as, for example, a polygon (e.g., square, rectangle, etc.), an oval, a circle, etc. In some embodiments, the matrix may be provided pre-trimmed in a desired shape of the support device.

In some embodiments, the matrix 302 may be a knitted and/or woven textile. In some embodiments, the matrix 302 may include weave, warp knits, and/or weft knits. In some embodiments, the body of the matrix 302 may be substantially inelastic when being positioned around the breast prosthesis (e.g., before implantation). In some embodiments, the support device, before or after implantation with the tissue expander into the patient, may stretch anisotropically over time. For example, the matrix may be configured to stretch in a first direction to a greater degree than in a second direction after the matrix 302 has been implanted into a patient. In some embodiments, the matrix 302 may have a suture pull-out force in a range of about 15 Newtons (N) to about 60 N in the warp direction and in a range of about 15 N to about 60 N in the weft direction, inclusive of all ranges and subranges therebetween. In some embodiments, the matrix 302 may have a suture pull-out force of greater than about 10 Newtons (N) in the warp direction and greater than 10 N in the weft direction. In some embodiments, the matrix 302 has a tensile strength in a range of about 100 N to about 450 N in the warp direction and in a range of about 100 N to about 450 N in the weft direction, inclusive of all ranges and subranges there between. In some embodiments, the matrix 302 has a minimum burst strength in a range of about 300 N to about 550 N, inclusive of all ranges and subranges therebetween. In some embodiments, the body of the matrix 302, after being implanted with the breast prosthesis into the patient, may be configured to allow tissue stretching over time to accommodate a size of the breast prosthesis.

In some embodiments, the matrix 302 may include one or more biocompatible, sterile materials. In some embodiments, the matrix 302 may include a synthetic material and/or a tissue matrix. In some embodiments, the matrix 302 may include an acellular tissue matrix. In some embodiments, the matrix 302 may include a substrate and/or a coating (e.g., a polymer coating). In some embodiments, the matrix 302 may include a bioabsorbable mesh substrate, a bioabsorbable polymer, and one or more active pharmaceutical ingredients (e.g., antibacterial agents antimicrobial agents, anesthetics, anti-inflammatory agents, anti-scarring agents, cancer treatment agents, anti-fibrotic agents, and/or leukotriene inhibitors). In some embodiments, the one or more active pharmaceutical ingredients may include can include one or a combination of active pharmaceutical ingredients, such as, for example, anesthetics, antibiotics, anti-inflammatory agents, procoagulant agents, fibrosis-inhibiting agents, anti-scarring agents, antiseptics, leukotriene inhibitors/antagonists, cell growth inhibitors and mixtures thereof.

In some embodiments, the polymer coating may contain antibacterial agents (e.g., antimicrobial such as antibiotics, antivirals, antifungals, antiparasitic). In some embodiments, the antibacterial agents may include, for example, Rifampin, Minocycline, Gentamycin, Vancomycin, Triclosan, Sirolimus, Ciprofloxacin, Levofloxacin, azithromycin, Rifabutin, Doxycycline, or a suitable combination thereof.

In some embodiments, one or more breast cancer treatment drugs may include, for example, Doxorubicin (Adriamycin), Epirubicin (Ellence), Taxanes, such as paclitaxel (Taxol) and docetaxel (Taxotere), 5-fluorouracil (5-FU) or capecitabine (Xeloda), Eribulin, Ixabepilone, Platinum agents (Cisplatin, carboplatin), Vinorelbine (Navelbine), Gemcitabine (Gemzar), Tamoxifen, Toremifene (Fareston), Fulvestrant (Faslodex), Elacestrant (Orserdu), Letrozole (Femara), Anastrozole (Arimidex), Exemestane (Aromasin), Luteinizing hormone-releasing hormone (LHRH) agonists such as goserelin (Zoladex) and leuprolide (Lupron), Monoclonal antibodies Trastuzumab, pertuzumab, hyaluronidase injection (Phesgo), Pertuzumab (Perjeta), and Margetuximab (Margenza), Anitbody-drug conjugates Ado-trastuzumab emtansine (Kadcyla) and Fam-trastuzumab deruxtecan (Enhertu), Kinase inhibitors Lapatinib (Tykerb) and Neratinib (Nerlynx), Tucatinib (Tukysa), CDK46 Inhibitors Palbociclib (Ibrance), ribociclib (Kisqali), and abemaciclib (Verzenio), mTOR inhibitor (Everolimis), PI3K inhibitor (alpelisib (Piquray)), Sacituzumab govitecan (Trodelvy), Olaparib (Lynparza), Talazoparib (Talzenna), and Pembrolizumab (Keytruda).

Examples of non-steroidal anti-inflammatories include, but are not limited to, naproxen, ketoprofen, ibuprofen as well as diclofenac; celecoxib; sulindac; diflunisal; piroxicam; indomethacin; etodolac; meloxicam; r-flurbiprofen; mefenamic; nabumetone; tolmetin, and sodium salts of each of the foregoing; ketorolac bromethamine; ketorolac bromethamine tromethamine; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, l, and racemic isomers); and the methyl, ethyl, propyl, isopropyl, n-butyl, sec-butyl, t-butyl, esters of acetylsalicylic acid.

Examples of anesthetics include, but are not limited to, licodaine, bupivacaine, and mepivacaine. Further examples of analgesics, anesthetics and narcotics include, but are not limited to acetaminophen, clonidine, benzodiazepine, the benzodiazepine antagonist flumazenil, lidocaine, tramadol, carbamazepine, meperidine, zaleplon, trimipramine maleate, buprenorphine, nalbuphine, pentazocain, fentanyl, propoxyphene, hydromorphone, methadone, morphine, levorphanol, and hydrocodone. Local anesthetics have weak antibacterial properties and can play a dual role in the prevention of acute pain and infection.

In some embodiments, the mesh substrate may include any suitable material including, for example, polylactic acid (PLA), polyglycolic acid (PGA), poly(L-lactide), poly(D,L-lactide), poly(L-lactide-co-D,L-lactide), poly(L-lactide-co-glycolide), poly(D,L-lactide-co-glycolide), poly(glycolide-co-trimethylene carbonate), poly(D,L-lactide-co-caprolactone), poly(glycolide-co-caprolactone), polyethylene oxide, polyoxaester, polypropylene fumarate, poly(ethyl glutamate-co-glutamic acid), poly(tert-butyloxy-carbonylmethyl glutamate), polyhydroxybutyrate, poly (phosphazene), poly(phosphate ester), poly(amino acid), polydepsipeptide, maleic anhydride copolymer, polyiminocarbonates, poly[(97.5% dimethyl-trimethylene carbonate)-co-(2.5% trimethylene carbonate)], poly(orthoesters), tyrosine-derived polyarylate, tyrosine-derived polycarbonate, tyrosine-derived polyiminocarbonate, tyrosine-derived polyphosphonate, polyalkylene oxide, hydroxypropylmethylcellulose, polydioxanone (PDO), prolyl 4-hydroxylase subunit beta (P4HB), polycaprolactone (PCL), polycaprolactone co-butylacrylate, polysaccharide, protein, polypropylene, expanded polytetrafluoroethylene or any other suitable material or combination thereof. In some embodiments, the mesh substrate may include a synthetic polyester derived from glycolic and lactic acids such as, for example, a porous matrix including multifilament or monofilament knitted mesh poly(glycolide-lactide) copolymer (PLGA). In some embodiments, the mesh substrate forms a macroporous scaffold, and the macroporous scaffold may act as a lattice for new tissue ingrowth that is neovascularized and remodeled as the fibers resorb.

In some embodiments, the mesh substrate may include a polymer coating including one or more active pharmaceutical ingredients. In some embodiments, the mesh substrate may be coated with a bioabsorbable polymer. For example, the support device may include a Tyrosine-based polyarylate coating containing antibacterial agents (e.g., Rifampin and Minocycline). The bioabsorbable polymer coating may be a naturally derived biodegradable polymer that degrades via bulk hydrolysis into natural metabolites. In some embodiments, the substrate and the polymer coating may be the same as or similar to the mesh prosthesis described in U.S. Pat. No. 9,987,116 titled "Temporarily Stiffened Mesh Prosthesis," filed Jul. 26, 2016, and U.S. Pat. No. 8,315,700 titled "Preventing Biofilm Formation on Implantable Medical Device," filed Dec. 28, 2009, the disclosures of each of which is hereby incorporated by reference in its entirety. In some embodiments, the matrix 302 may be a sterile, synthetic, macroporous, and/or knitted scaffold comprised of a bioabsorbable copolymer including at least one of glycolide and lactide substrate and coated with a bioabsorbable tyrosine-based polyarylate.

The antibacterial agents may include at least one of Rifampin and Minocycline. In some embodiments, a concentration of Rifampin may be in a range of about 20 mg to about 180 mg, inclusive of all ranges and subranges therebetween. In some embodiments, a concentration of Minocycline may be in a range of about 20 mg to about 180 mg, inclusive of all ranges and subranges therebetween. In some embodiments, the antibacterial agents may include concentrations of Rifampin in a range of about 60 mg to about 100 mg and/or may include concentrations of Minocycline in a range of about 40 mg to about 70 mg. In some embodiments, the antibacterial agents a patient may receive may be no greater than 180 mg Rifampin and 180 mg Minocycline. In some embodiments, a concentration of the antibacterial agents provided by the matrix 302 may be no greater than a recommended daily dose, e.g., the recommended daily oral dose for Rifampin is 600 mg/day and for Minocycline is 200 mg/day. In some embodiments, the dosage specifications may be anywhere from 80-120% of the following dosages: 84.7 mg rifampin and 54.3 mg Minocycline. In some embodiments, the dosage may be in a range of about 67.8 mg to about 101.6 mg Rifampin and about 43.4 to about 65.2 mg Minocycline.

In some embodiments, the support device may be uniformly coated across the surface area of the support device. In some embodiments, the polymer coating may be operable to control the release of the antibacterial agents (e.g., Rifampin and Minocycline) present on the matrix 302 in uniform concentrations across the surface area over the course of several days. In some embodiments, the polymer coating may be operable to control the release of the antibacterial agents present on the matrix 302 in concentrations of about 90-120 $\mu g/cm^2$ and about 50-80 $\mu g/cm^2$, respectively, over the course of several days. In some embodiments, the Rifampin may be present on the matrix 302 in a concentration in a range of about 20 $\mu g/cm^2$ to about 200 $\mu g/cm^2$. In some embodiments, the Minocycline may be present on the matrix in a concentration in a range of about 5 $\mu g/cm^2$ to about 100 $\mu g/cm^2$. In some embodiments, the concentration of Rifampin may be greater than the concentration of Minocycline. The polymer/drug coating is uniformly coated across the matrix, 302 and the drug dosage may correlate to the surface area of the matrix 302.

In some embodiments, the polymer coating is absorbable by the human body. In some embodiments, the coating may act as a carrier for the antibacterial agents. In some embodiments, the matrix 302 may release the antibacterial agents after implantation to reduce risk of infection at the surgical site. In some embodiments, the support device may provide antibacterial activity against *Staphylococcus aureus*, methicillin-resistant *Staphylococcus aureus* (MRSA), *Staphylococcus epidermidis*, methicillin-resistant *Staphylococcus Epidermis* (MRSE), *Pseudomonas aeruginosa*, *Escherichia coli* (*E. coli*) and *Klebsiella pneumoniae*, and *Acinetobacter baumannii*.

In some embodiments, the matrix 302 described herein can be unique from other ADMs and synthetic meshes in terms of tissue interaction and absorption time. In existing ADMs, the tissue ingrowth begins from the tissue-contacting side and moves toward the prosthesis through an enzymatic reaction that requires tissue contact. In some embodiments, the matrix 302 when trimmed into the support device and implanted may be configured to allow or cause tissue ingrowth and tissue infiltration into the substrate whereby cells can migrate through the pores to form new tissue around the support device. In some embodiments, the matrix 302 can absorb by the process of hydrolysis over approximately nine weeks, promoting full absorption of the matrix 302, regardless of tissue contact, because the matrix is in an aqueous environment when implanted. In some embodiments, the matrix 302 may be absorbed over a timeframe of a few weeks (e.g., 3-4 weeks) to about twelve months, inclusive of all ranges and values therebetween. As the matrix 302 provides a scaffold for cell adhesion, collagen formation, and/or subsequent collagen maturation, the matrix 302 can also provide support to the soft tissue during the tissue expansion process. Furthermore, the pliability of the matrix 302, while retaining mechanical strength as it absorbs or integrates during the acute implantation period, can allow for continued expansion of the breast pocket without interference.

In some embodiments, a kit may include the matrix 302 and the foldable sheet 304 including one or more templates. The foldable sheet may be configured to be folded into an envelope form that is configured to enclose around the matrix 302 to maintain the matrix in a sterile environment therein. The foldable sheet 304 may include the partial support template configured for use in shaping the matrix into a first support device configured to provide partial coverage for a breast prosthesis, and a full support template configured for use in shaping the matrix into a second support device configured to provide full coverage for a breast prosthesis.

As shown in FIG. 3B, the foldable sheet 304 when folded into the envelope may be disposed in a pouch 350 (e.g., a foil pouch). In some embodiments, after the envelope is disposed in the foil pouch 350, the pouch 350 may be sterilized, sealed, and labeled prior to insertion into a secondary package (e.g., a cardboard box). In some embodiments, the matrix 302, the foldable sheet 304, and/or the pouch 350 may be sterilized using gamma irradiation or electron-beam.

Figure 4:
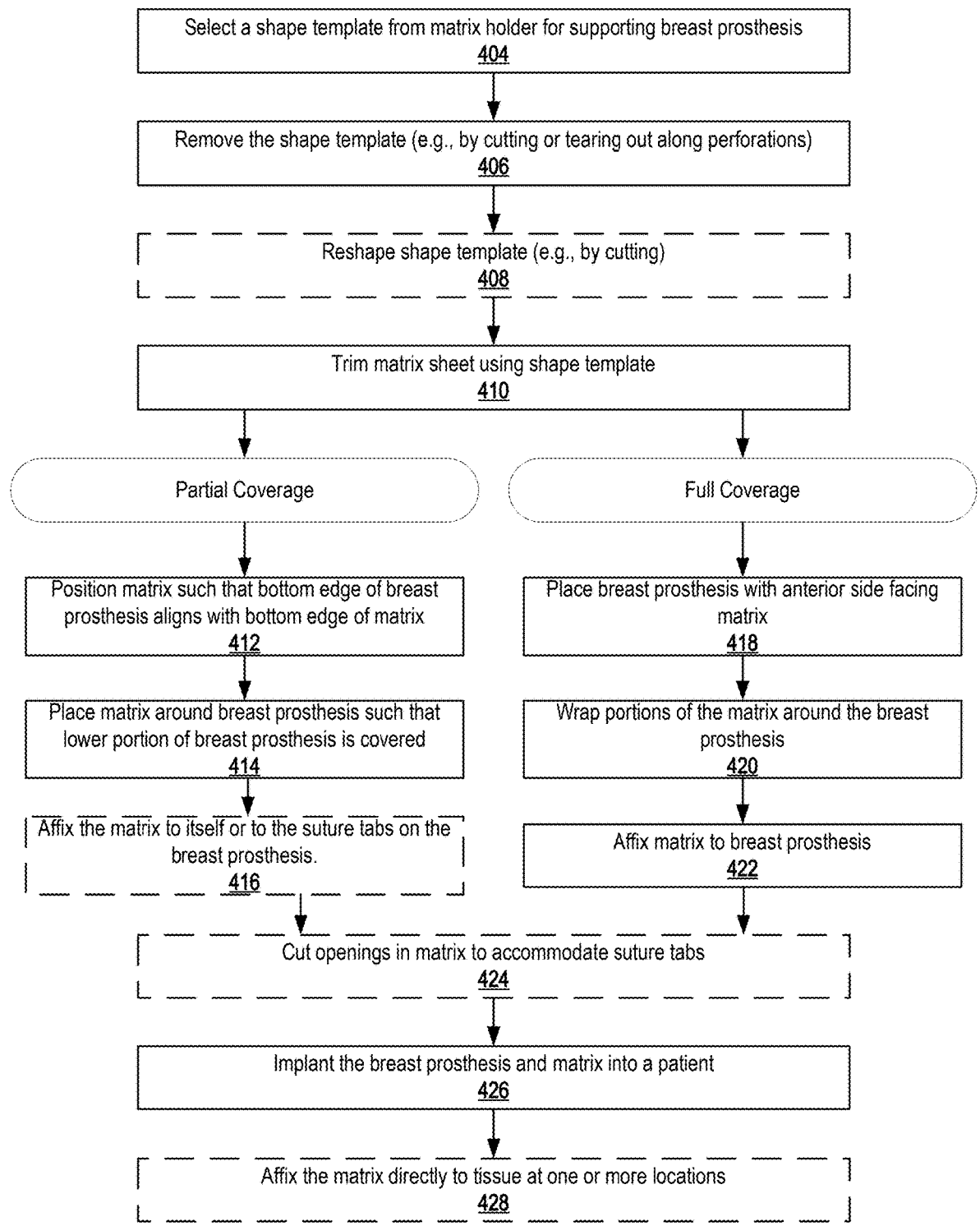
FIG. 4 is a flowchart of a method of using a matrix holder to shape a matrix sheet, for supporting a breast prosthesis, according to embodiments.

FIG. 4 is a flowchart of a method of using a matrix holder to shape a matrix, for supporting a breast prosthesis, according to embodiments. In some embodiments, the matrix holder may be disposed in a sterilized foil pouch, and the matrix holder may be removed from the foil pouch using aseptic technique. In some embodiments, the matrix holder may be unfolded, and the matrix may be aseptically removed from the matrix holder. The method 400 may include selecting a shape template from a matrix holder for supporting a breast prosthesis, at 404. In some embodiments, the matrix holder may include perforations along a portion of the matrix holder such that the shape template can be removed from the matrix holder along the perforations. In some embodiments, the matrix holder may include one shape template. In some embodiments, the matrix holder may include more than one shape template. For example, the matrix holder may include a shape template corresponding to a partial coverage support device and a shape template corresponding to a full coverage support device. In some embodiments, the matrix holder may include shape templates having different sizes. For example, the matrix holder may include a shape template for a first (e.g., medium size) partial coverage support device and a shape template for a second (e.g., large size) partial coverage support device and/or a shape template for a medium full coverage support device and a shape template for a large full coverage support device. In some embodiments, the large partial coverage support device may be most effectively used with a breast prosthesis having a size greater than 600 cc. In some embodiments, the medium partial coverage support device may be most effectively used with a breast prosthesis having a size smaller than 600 cc. In some embodiments, the full coverage support device may be most effectively used with a breast prosthesis having a size 500 cc or larger.

At 406, the shape template may be provided within but unattached from the matrix holder or may be removed from the matrix holder (e.g., by breaking, cutting or tearing along perforations). In some embodiments, the perforations may be configured such that the user can easily cut or tear the matrix holder material along the perforations. At 408, the method 400 optionally includes reshaping the shape template (e.g., by cutting). In some embodiments, prior to cutting the matrix, the shape template can be modified to accommodate an anatomy of the patient and/or a structure (e.g., size or shape) of the breast prosthesis. In some embodiments, excess material may be removed from the shape template such that the matrix can be trimmed to a shape that better fits in the breast pocket of the patient. At 410, the matrix can be trimmed using the shape template to produce a support device. In some embodiments, the matrix may be trimmed (e.g., cut, torn, etc.) according to the shape template. In some embodiments, the shape template may be disposed on the matrix, and the matrix may be trimmed along a perimeter of the shape template. In some embodiments, the matrix holder may include one or more sets of printed lines, and the user may trace the support device along a set of printed lines. In some embodiments, after the matrix is trimmed using the shape template, the matrix may be further trimmed or reshaped to the desired shape and/or size. In some embodiments, the matrix may be shaped or trimmed without using the shape template. In some embodiments, the matrix may not be trimmed smaller than one eighth of a starting size of the matrix.

The support device may be positioned to cover at least a portion of the breast prosthesis. For the partial coverage support device, the matrix may be positioned such that a bottom edge or pole of the breast prosthesis aligns with a bottom edge of the matrix, at 412. For example, the matrix may be a crescent shape or semi-circular shape and configured such that a rounded edge of the crescent or semi-circle is aligned with a bottom edge of the breast prosthesis. At 414, the matrix may be wrapped around the breast prosthesis such that a lower portion of the breast prosthesis is covered. At 416, the matrix may be optionally affixed to the breast prosthesis or around the breast prosthesis. For example, the matrix may be sutured to itself around the breast prosthesis or sutured to the suture tabs on the breast prosthesis.

For the full coverage support device, the breast prosthesis may be positioned with an anterior side of the breast prosthesis facing the matrix, at 418. At 420, portions of the matrix may be wrapped around the breast prosthesis. For example, the matrix may have four extensions (e.g., petals) that may be wrapped around the breast prosthesis. In some embodiments, extensions opposite one another may be joined on a posterior side of the breast prosthesis. In some embodiments, the extensions or petals may be coupled to one another on the posterior side of the breast prosthesis (e.g., via sutures, an adhesive, etc.). At 422, the matrix may be affixed to the breast prosthesis. For example, the matrix may be sutured or adhered via an adhesive to the breast prosthesis.

The method 400 may optionally include cutting one or more openings in the matrix to accommodate suture tabs of the breast prosthesis, at 424. For example, one or openings may be created along a portion of the support device corresponding to a perimeter of the breast prosthesis. At 426, the breast prosthesis and support device may be implanted into the patient. In some embodiments, the breast prosthesis and support device may be implanted concurrently. In some embodiments, the breast prosthesis and/or the support device may be affixed to the surrounding tissue during implantation at one or more locations, at 428. In some embodiments, the support device may be affixed to the surrounding tissue via one or more extensions of the matrix and/or the breast prosthesis may be fixed to surrounding tissue via the suture tabs of the breast prosthesis.

Figure 5:
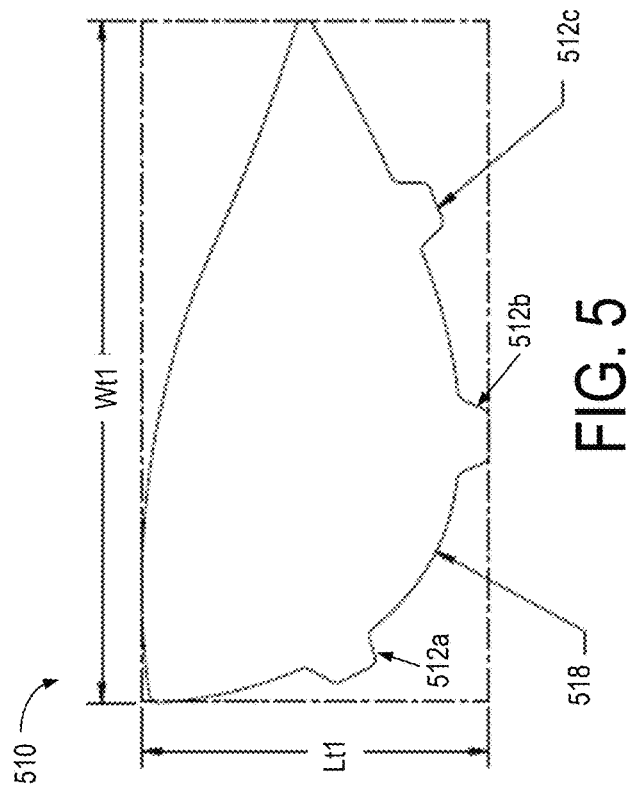
FIG. 5 depicts a template for shaping a support device for supporting a breast prosthesis, according to embodiments.

FIG. 5 shows a shaped component 510 such as a support device or template for partial coverage support, according to an embodiment. Some aspects of the shaped component 510 may be structurally and/or functionally similar to the support device and/or templates described herein, and therefore certain aspects of the shaped component 510 are not described herein with respect to FIG. 5. In some embodiments, the shaped component 510 can be a template used to cut a matrix into a support structure that can be used as lower pole support or a subpectoral sling (e.g., a partial support device). In some embodiments, the shaped component 510 can be a pre-shaped support device. The shaped component 510 may be more effectively used with breast prostheses larger in size. The shaped component 510 may include a central region 518 and three extensions 512a, 512b, 512c. In embodiments, the width Wt1 can be between about 250 mm (25 cm) and about 350 mm (35 cm), inclusive of all sub-ranges and values therebetween, and the length Lt1 can be between about 100 mm (10 cm) and about 200 mm (20 cm), inclusive of all sub-ranges and values therebetween. As shown, the width Wt1 can be about 280 mm (28 cm), and the length Lt1 can be about 143 mm (14.3 cm). In some embodiments, a radius of curvature of the central region 528 of the shaped component, may depend on a size of the breast prosthesis with which the support device is implanted. In some embodiments an average curvature of a bottom edge of the central region 518 of the shape, and therefore an average curvature of a bottom edge of the central region of the support device may correspond to a curvature of the breast prosthesis. In some embodiments an average radius of the central region 518 of the shaped component may be in a range of about 0.5 to about 2.0, inclusive of all ranges and subranges therebetween.

Figure 6:
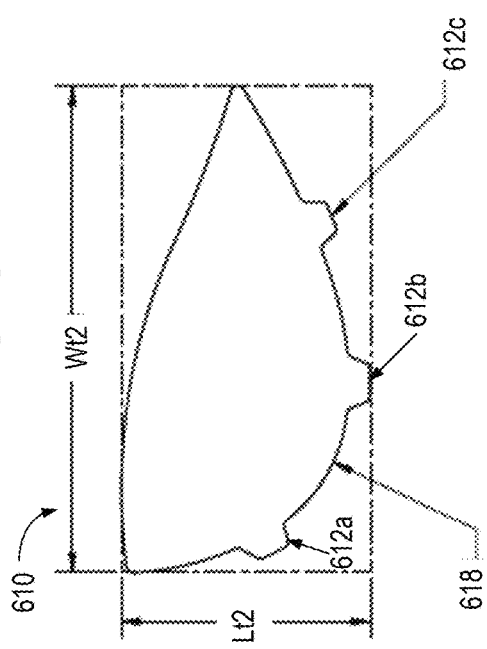
FIG. 6 depicts a template for shaping a support device for supporting a breast prosthesis, according to embodiments.
Figure 7:
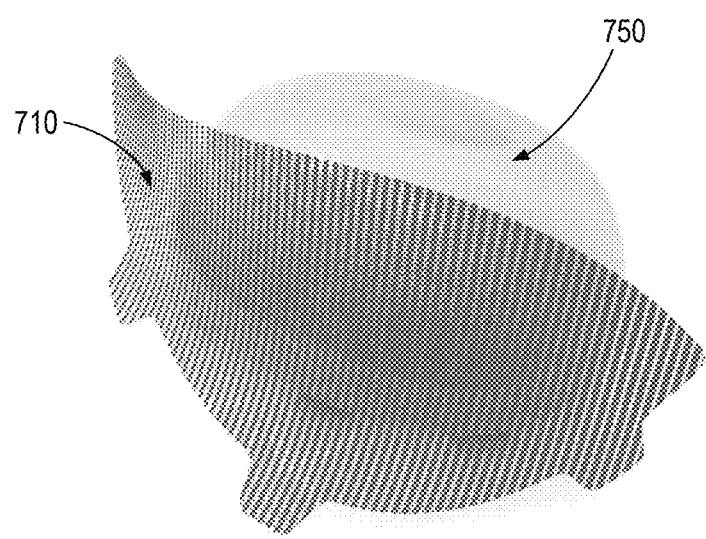
FIG. 7 depicts a support device that provides partial support being placed around a breast prosthesis, according to embodiments.

FIG. 6 shows a shaped component 610 such as a support device or template for partial coverage support. Some aspects of the shaped component 610 may be structurally and/or functionally similar to the support devices and/or templates described herein, and therefore certain aspects of the shaped component 610 are not described herein with respect to FIG. 6. The shaped component 610 may be more effectively used with breast prostheses smaller in size. The shaped component 610 may include a central region 618 and three extensions 612a, 612b, 612c. In embodiments, the width Wt2 can be between about 150 mm (15 cm) and about 250 mm (25 cm), inclusive of all sub-ranges and values therebetween, and the length Lt2 can be between about 50 mm (5 cm) and about 150 mm (15 cm), inclusive of all sub-ranges and values therebetween. As shown, the width Wt2 can be about 200 mm (20 cm) and the length Lt2 can be about 102 mm (10.2 cm). In some embodiments an average curvature of a bottom edge of the central region 628 of the shaped component may correspond to a curvature of the breast prosthesis. In some embodiments an average radius of the central region 628 of the shaped component may be in a range of about 0.5 to about 2, inclusive of all ranges and subranges therebetween. FIG. 7 depicts a support device 710 that provides partial support being placed around a breast prosthesis 750, according to embodiments. As shown, the shape of the support device 710 includes a crescent shape with extensions, the shape corresponding to the shape of the shaped components(s) in FIGS. 5-6. As shown, the support device 710 may be wrapped around a bottom pole of the breast prosthesis 750. In some embodiments, the partial support device including the crescent shape may be used for unilateral procedures and/or for submuscular implant procedures.

Figure 8:
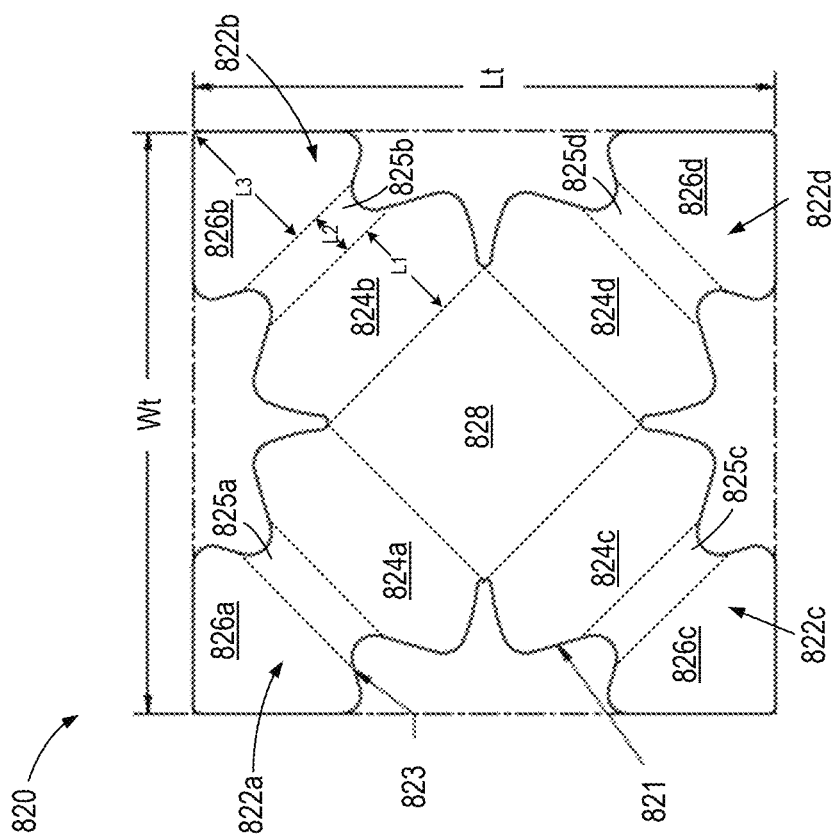
FIG. 8 depicts a template for shaping a support device for supporting a breast prosthesis, according to embodiments.

FIG. 8 depicts a shaped component 820 for such as a support device or template for supporting a breast prosthesis, according to embodiments. Some aspects of the shaped component 820 may be structurally and/or functionally similar to the support devices and/or templates described herein, and therefore certain aspects of the shaped component 820 are not described herein with respect to FIG. 8. As shown, the shaped component includes a central portion 828 and a plurality of extensions 822a, 822b, 822c, 822d extending from the central portion 828. Each extension 822a-822d includes a first section 824a, 824b, 824c, 824d, a second section 825a, 825b, 825c, 825d, and a third section 826a, 826b, 826c.

In some embodiments, a width Wt of the shaped component may be defined between (1) an apex of the first extension 824a and an apex of the second extension 824b and (2) an apex of the third extension 822c and an apex of the fourth extension 822d. A length Lt of the shaped component 820 may be defined between (1) an apex of the first extension 822a and an apex of the third extension 822c and (2) an apex of the second extension 822b and an apex of the fourth extension 822d. In some embodiments, the width Wt of the shaped component is equal to the length Lt of the shaped component. In embodiments, the width Wt and the length Lt can be between about 150 mm (15 cm) and about 400 mm (40 cm), including all sub-ranges and values therebetween. In some embodiments, the width Wt and the length Lt can be between about 250 mm (25 cm) to about 360 mm (36 cm), inclusive of all ranges and subranges therebetween. In some embodiments, the width Wt can be about 260 mm (26 cm), and the length Lt can be about 260 mm 26 (cm). The shaped component can be designed so that one or more corners of the support structure, can be wrapped around an implant (e.g., a tissue expander, a breast prosthesis, etc.) without creating overlapping regions (or significant overlapping regions). For example, the shaped component may be configured such that when the extensions of the support device are wrapped around the breast prosthesis, the extensions have no more than about 10%, no more than about 20%, no more than about 30%, no more than about 40%, no more than about 50% overlap with each neighboring extension.

In some embodiments, the first section 824a-824d, second section 825a-825d, and third sections 826a-826d of each extension 822a-822d may form continuous curves that extend from the central region and terminate at the apex of each of the plurality of extensions 822a-822d. As shown, the third section of the shaped component 820 may increase to a greater width than that of the second section 825a-825d before tapering to an apex. The third section of the support device may be configured to cover at least a portion of a posterior side of the breast prosthesis, and the apex of each of the plurality of extensions of the support device may be configured to be coupled to one another at the posterior side of the breast prosthesis to secure the body of the support device to the breast prosthesis. In some embodiments, a maximum width of the third section of the shaped component 820, and therefore a maximum width of the third section the support device, is smaller than a maximum width of the first section 824a-824d of each of the extensions 822a-822d. In some embodiments, the maximum width of the first section 824a-824d of each extension 822a-822d may be greater than a maximum width of the second section 825a-825d of each extension and the maximum width of the third section 826a-826d of each extension 822a-822d. In each of these instances, the maximum width can be measured as the lateral length of the section, measured perpendicularly to a longitudinal axis of the extension.

In some embodiments, the maximum width of the extension (e.g., the maximum width of the first section 824a-824d of each extension 822a-822d) is in a range of about 10% (¹⁄₁₀) of the total width Wt to about 60% (⅗) of the total width Wt, inclusive of all ranges and subranges therebetween. In some embodiments, the maximum width of the extension (e.g., the maximum width of the first section 824a-824d of each extension 822a-822d) is in a range of about 25% (or ¼) of the total width Wt to about 50% (or ½) of the total width Wt, inclusive of all ranges and subranges therebetween. In some embodiments, the first section 824a-824d may have a length L1 in a range of about 45 mm to about 55 mm, inclusive of all ranges and subranges therebetween. In some embodiments, a minimum width of the second section 825a-825d of each extension 822a-822d may be in a range of about 230 mm to about 290 mm, inclusive of all ranges and subranges therebetween. In some embodiments, the second section 825a-825d may have a length L2 in a range of about 15 mm to about 20 mm, inclusive of all ranges and subranges therebetween. In some embodiments, the maximum width of the third section 826a-826d of each extension 822a-822d may be in a range of about 230 mm to about 290 mm, inclusive of all ranges and subranges therebetween. In some embodiments, the third section 826a-826d may have a length L3 in a range of about 60 mm to about 70 mm, inclusive of all ranges and subranges therebetween. In some embodiments, a total length of each extension 822a-822d may equal L1+L2+L3. In some embodiments, a total length of each extension 822a-822d may be in a range of about 10% of the total length of the shaped component Lt to about 60% of the total length of the shaped component Lt, inclusive of all ranges and subranges therebetween. In some embodiments, the total length of each extension 822a-822d may be in a range of about 50% of the total length of the shaped component Lt. Therefore, the total length of each extension may be in a range of about 120 mm to about 145 mm, inclusive of all ranges and subranges therebetween. As shown, the central region 828 be a square or rectangle and may have a length and a width. In some embodiments, the length and/or the width of the central region 828 may be in a range of about 90 mm to about 110 mm, inclusive of all ranges and subranges therebetween.

In some embodiments, each extension (e.g., the width and length) may have dimensions that allow the extensions to collectively cover the surface area of breast implants of various sizes including large sizes such as, for example, 1000 cc-1400 cc.

Figure 9:
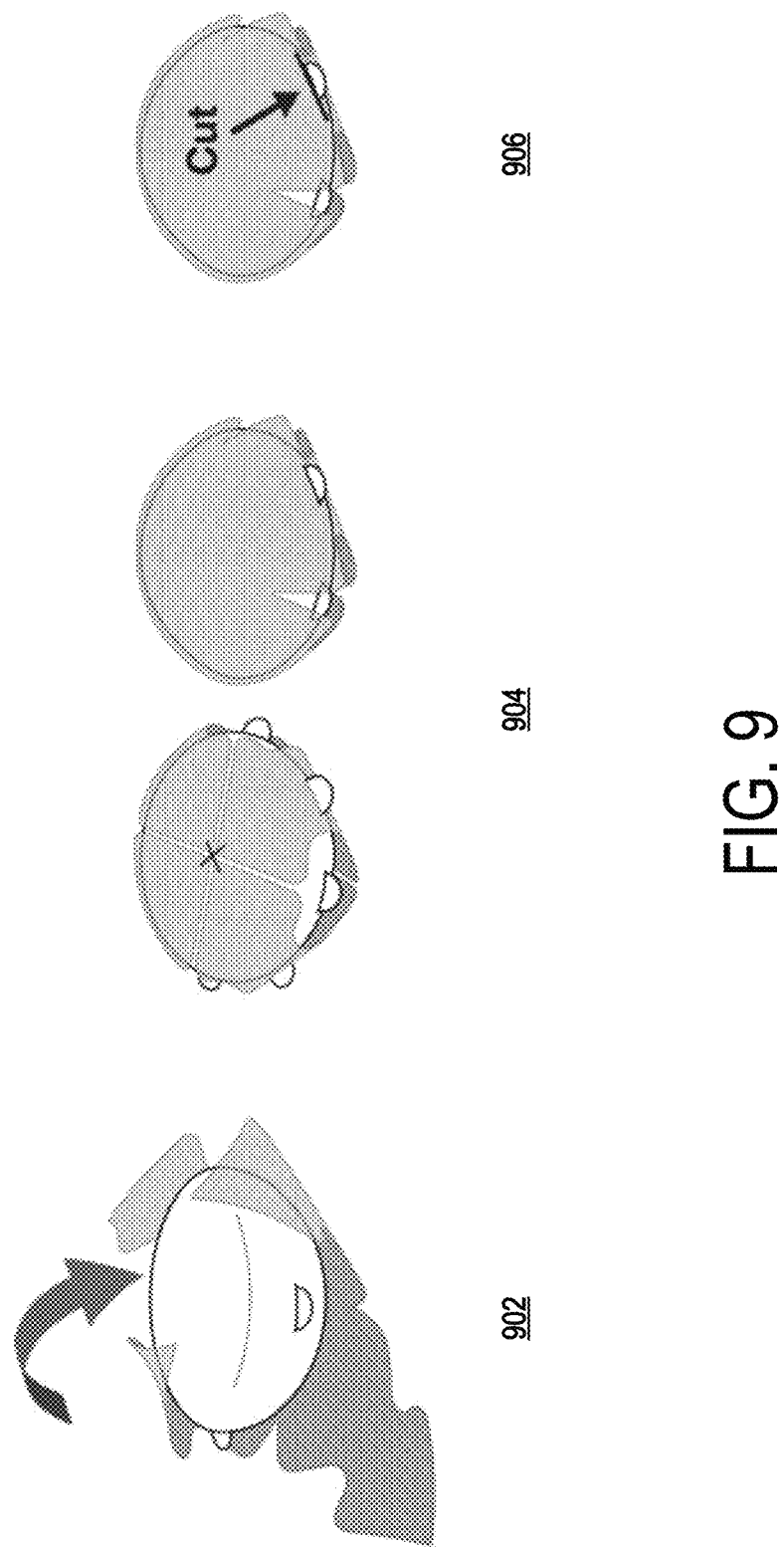
FIG. 9 depicts a method of placing a support device around a breast prosthesis, according to embodiments.

FIG. 9 depicts a method of placing a support device around a breast prosthesis, according to embodiments. As shown in 902, an anterior side (e.g., port side) of a breast prosthesis may be disposed on a central portion of the support device, and each of the extensions may be wrapped around the breast prosthesis from the anterior side to a posterior side of the breast prosthesis. At 904, the apex of opposing extensions may be coupled to one another to secure the support device around the breast prosthesis. At 906, one or more openings or slots may be cut in the matrix such that extensions on the breast prosthesis may be disposed therethrough such that the extensions on the breast prosthesis may be affixed to a tissue in the patient during implantation.

Figure 10A:
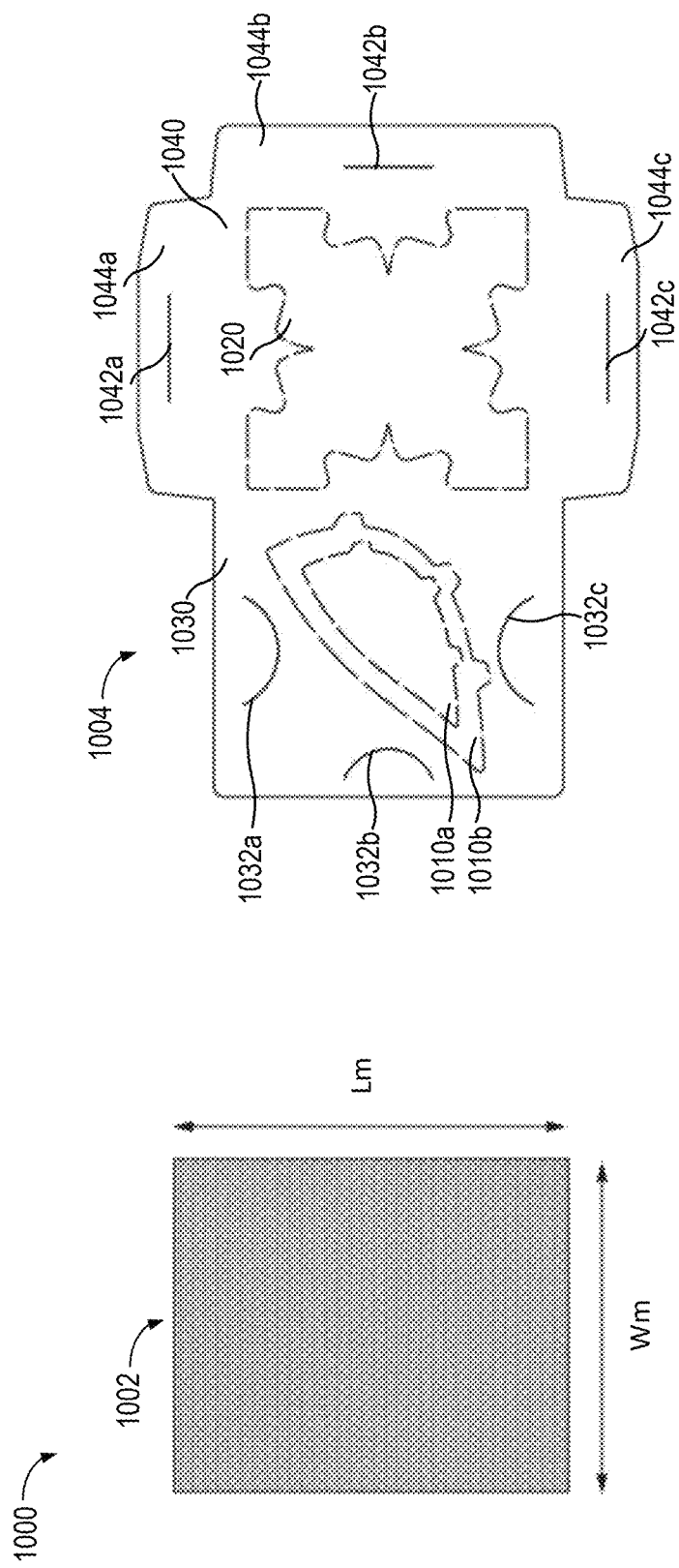
FIG. 10A depicts a holder configured to hold or enclose a matrix sheet, which can be shaped into a support device for supporting a breast prosthesis, according to embodiments.

FIG. 10A depicts a matrix holder 1000 configured to hold or enclose a matrix sheet 1002, which can be shaped into a support device for supporting a breast prosthesis, according to embodiments. The matrix holder 1000 can be structurally and/or functionally similar to the holders described in FIGS. 3A-3B. As shown, the matrix holder 1000 includes a foldable sheet 1004 including a first section 1030 and a second section 1040. The first section includes 1030 a first partial support device template 1010a and a second partial support device template 1010b bigger. The first and second partial support device templates 1010a, 1010b form a crescent-like shape. As shown, the templates are arranged such that the first partial support device template 1010a is disposed in an area defined by the second partial support device template 1010b. The first section 1030 further includes three tabs 1032a, 1032b, 1032c. The tabs 1032a-1032 may be formed by separating (e.g., cutting or tearing) a portion of the foldable sheet 1004 such that a portion of the foldable sheet 1004 may be pulled out of plane with the foldable sheet 1004. As shown, the tabs 1032a-1032c are semi-circular tabs formed by creating an arced cut or incision. The first tab 1032a is arranged near a top edge of the first section 1030 and centered along a width of the first section 1030. The second tab 1032b is arranged near a side edge of the first section 1030 and centered along a length of the first section 1030. The third tab 1032c is arranged near a bottom edge of the first section 1030 and centered along a width of the first section 1030. The second section 1040 includes a full support device template 1020. As shown, the full support device template 1020 includes a symmetrical flower or cross shape having four extensions. The second section 1040 further includes three extensions 1042a, 1042b, 1042c, each extension defining a respective slot 1042a, 1042b, 1042c.

In some embodiments, a length LS of the second section 1040 (not including extensions 1044a, 1044c) and a length of the first section 1030 is in a range of about 300 mm to about 360 mm, including all ranges and subranges therebetween. In some embodiments, a length LS is about 332.6 mm. In some embodiments, a length LES of the second section 1040 including extensions 1044a and 1044c in a range of about 430 mm to about 490 mm, including all ranges and subranges therebetween. A length LE of the extensions 1044a and 1044b is in a range of about 65 mm to about 95 mm, including all ranges and subranges therebetween. In some embodiments, a width WS of the second section 1040 (not including extensions 1044b) is in a range of about 250 mm to about 310 mm, including all ranges and subranges therebetween. In some embodiments, a total width WTS of the foldable sheet 1004 is in a range of about 595 to about 655, including all ranges and subranges therebetween. In some embodiments, the extensions 1044a-1044c extend an entire length of a respective edge of the second section 1040. In some embodiments, the extension 1044a-1044c may not extend an entire length of the respective edge of the second section 1040.

In some embodiments, a distance DS1 between the slits 1042a, 1042c, and an edge of the top and bottom extensions 1044a, 1044c is in a range of about 15 mm to about 40 mm, including all ranges and subranges therebetween. In some embodiments, a distance DS2 between the slit 1042b and the side edge of the side extension 1044b is in a range of about 25 mm to about 55 mm, inclusive of all ranges and subranges therebetween. In some embodiments, a minimum distance DT2 between the tabs 1032a, 1032c, and an edge of the top and bottom tabs is in a range of about 10 to about 30, including all ranges and subranges therebetween. In some embodiments, a minimum distance DT1 between the tab 1032b and the side edge of the second section 1040 is in a range of about 5 mm to about 25 mm, inclusive of all ranges and subranges therebetween.

Figure 10B:
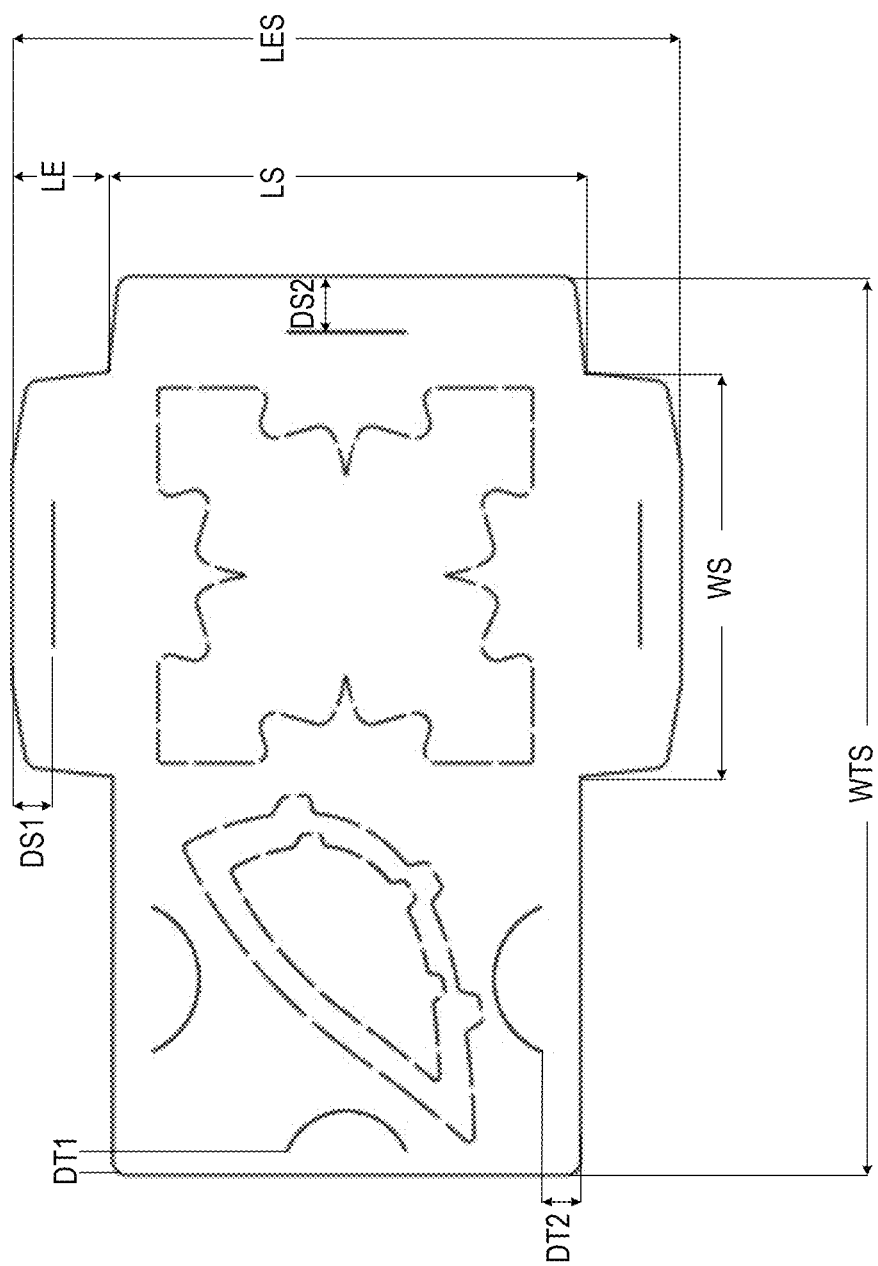
FIG. 10B depicts the holder of FIG. 10A with dimensions labeled.

As shown in FIG. 10B, the first section 1030 of the foldable sheet 1004 may be folded over the second section 1040 such that the matrix 1002 may be disposed between the first section 1030 and the second section 1040. After folding the foldable sheet 1004, the tabs 1032a-1032c on the first section may be disposed through the slots 1042a-1042c on the extensions 1044a-1044c of the second section 1040 to secure the matrix 1002 in the envelope, as shown in FIG. 10B.

Figure 11:
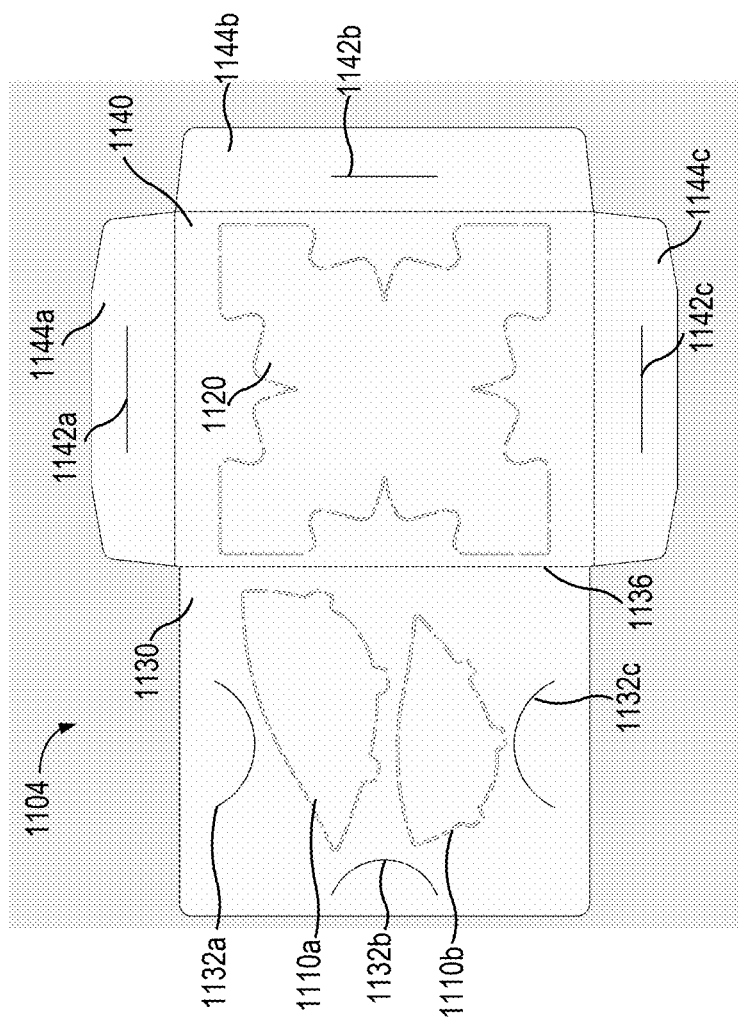
FIG. 11 depicts a holder configured to hold or enclose a matrix sheet, which can be shaped into a support device for supporting a breast prosthesis, according to embodiments.

FIG. 11 depicts a holder configured to hold or enclose a matrix sheet, which can be shaped into a support device for supporting a breast prosthesis, according to an embodiment. The foldable sheet 1104 may be structurally and/or functionally similar to any foldable sheet described herein, and therefore, certain details of the foldable sheet 1104 are not described again with respect to FIG. 11. As shown, the matrix holder includes a foldable sheet 1104 having a first section 1130 and a second section 1140. The first section 1130 includes a first partial coverage support device template 1110a and a second partial coverage support device template 1110b arranged adjacent to (e.g., above and below) one another. As shown, the template 1110a is positioned above the template 1110b, and the templates 1110a, 1110b are arranged to horizontally mirror one another. The first section 1130 further include three tabs 1132a, 1132b, 1132c. The second section 1140 includes a full coverage support device template 1120 and is coupled to three extensions 1144a, 1144b, 1144c. Each extension 1114a-1144c defines a slot through which the tabs 1132a-1132c may be disposed when the foldable sheet 1104 is folded.

Figure 12B:
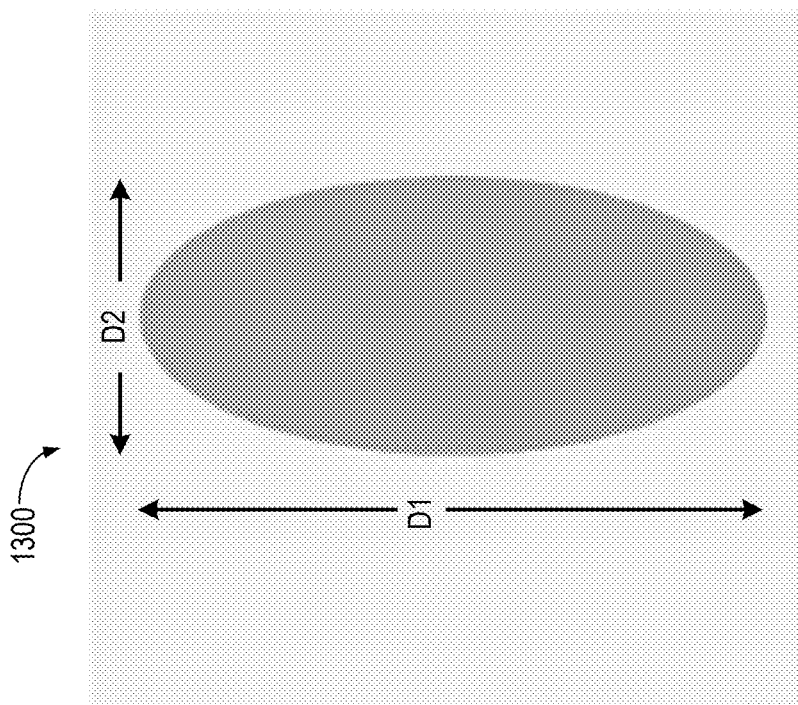
FIGS. 12A-12B depict support devices for supporting a breast prosthesis, according to embodiments.
Figure 12A:
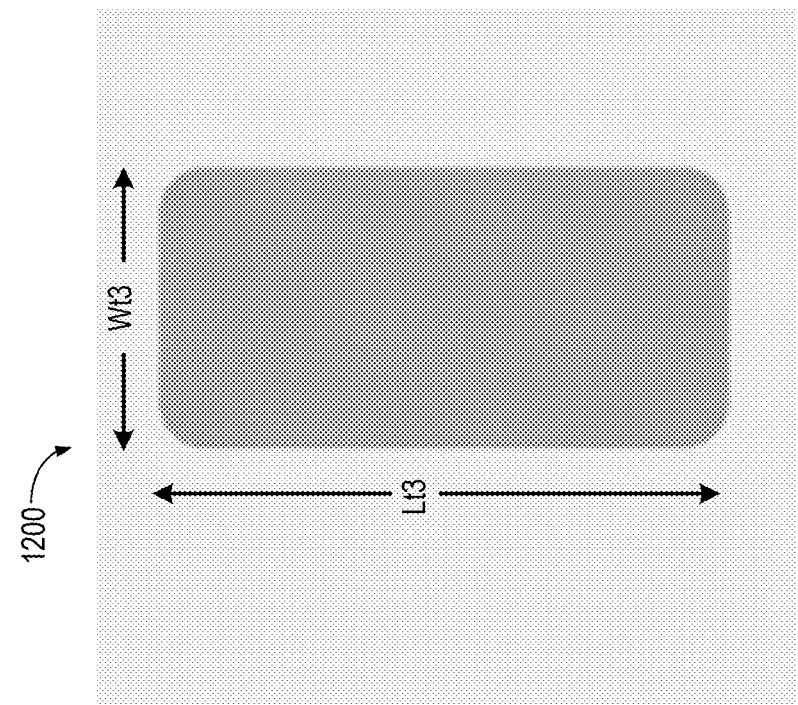

FIG. 12A depicts a support device 1200 for breast prosthesis having a rectangular shape, according to embodiments. As shown, the support device 1200 may be formed in a rectangle with rounded edges. In some embodiments, the rectangle may not include rounded edges. The rectangle may have a length Lt3 and a width Wt3. In some embodiments, the length Lt3 may be in a range of about 160 mm (16 cm) to about 320 mm (32 cm), inclusive of all ranges and subranges therebetween. In some embodiments, the length Lt3 may be in a range of about 230 mm (23 cm) to about 260 mm (26 cm), inclusive of all ranges and subranges therebetween. In some embodiments, the width Wt3 may be in a range of about 50 mm (5 cm) to about 230 mm (23 cm) inclusive of all ranges and subranges therebetween. In some embodiments, the width Wt3 may be in a range of about 110 mm (11 cm) to about 170 mm (17 cm), inclusive of all ranges and subranges therebetween. The support device may come in two sizes. For example, the first size of the support device 1200 may have a length Lt3 of 230 mm (23 cm) and a width Wt3 of 110 mm (11 cm). In some embodiments, the second size of the support device 1200 may have a length Lt3 of 260 mm (26 cm) and a width Wt3 of 170 mm (17 cm). In some embodiments, the rectangular support device 1200 may be used for lower pole support in submuscular or prepectoral implant procedures. In some embodiments, the rectangular implant may be used to tent the anterior side of the breast prosthesis in prepectoral procedures.

FIG. 12B depicts a support device 1300 for breast prosthesis having an oval shape, according to embodiments. In some embodiments, the support device 1300 may have a first diameter D1 and a second diameter D2. The first diameter D1 and the second diameter D2 may be in a range of about 140 mm (14 cm) to about 330 mm (33 cm), inclusive of all ranges and subranges therebetween. In some embodiments, the first diameter D1 and the second diameter D2 may be in a range of about 200 mm (20 cm) to about 270 mm (27 cm), inclusive of all ranges and subranges therebetween. In some embodiments, the oval support device 1300 may come in various sizes. In some embodiments, the oval support device 1300 may be used for cosmetic procedures.

The length Lt3 of the support device 1200 and the diameter D1 of support device 1300 may correspond to a length of the surgical pocket of the breast. For example, the length Lt3 and/or the diameter D1 may accommodate a length above and below the height of the breast implant to accommodate various sizes. The width Wt3 of support device 1200 and the diameter D2 of support device 1300 may be configured to cover the width of the surgical pocket of the breast and/or the width of the breast implant.

While the embodiments disclosed herein describe templates that are used for shaping one or more matrix materials, it can be appreciated that such matrix materials can be pre-formed or pre-shaped in the shape of the templates as shown in, for example, FIGS. 2A, 2B, 5, 6, 8, and 12. For example, the matrix materials may be pre-shaped (e.g., cut) into a full support device and/or a partial support device. In some embodiments, the matrix materials may be pre-cut into a desired shape (e.g., any of the template shapes described herein) using any suitable method including, for example, laser cutting and/or cutting via heated die. In some embodiments, one or more pre-shaped matrix materials may be disposed in a foldable sheet (e.g., similar to the foldable sheet 304). In some embodiments, a kit may include a foldable sheet and at least one of a matrix material pre-shaped into a full support device and a matrix material pre-shaped into a partial support device. The foldable sheet may be configured to be folded into an envelope form that is configured to enclose around the pre-formed matrix material to maintain the pre-formed matrix material in a sterile environment therein.

Summary of Findings from Studies 3.1 GLP Animal Study

An animal study was conducted to demonstrate safety of using a support device formed from the matrices described herein (e.g., matrix 100) by comparing the tissue response of a representative large tissue expander to a tissue expander covered with support device in a breast reconstruction model. Devices were implanted with a tissue expander without any support device on one side and a tissue expander covered with the full coverage support device on the contralateral side. It was then affixed to the tissue expander, and the tissue expander was affixed to the surgical pocket. Each expander was filled and additional fills were done post implantation. Table 5 summarizes the evaluations conducted during the implantation period.

TABLE 5

Evaluations Conducted During Implantation Period

| Evaluation | Frequency |
| --- | --- |
| Complete Blood Count (CBC) Serum Chemistry Plasma | Pre-surgery, post implantation, pre- termination |
| General health and incision site evaluation | Daily through 35 days post implantation |
| Comprehensive incision evaluation (under anesthesia): Seroma Dehiscence and repair Device migration Abnormalities | two time points post implantation |
| Weight | Pre-surgery, post implantation, pre- termination |

Following the implantation period, 5 animals were euthanized at multiple time points after implantation, prior to full absorption and after full absorption. A comprehensive necropsy was performed and two capsules were harvested, from which histology samples were taken. Additionally, capsule samples were harvested for mechanical testing.

The study demonstrated the safety of the support device. All animals survived to their assigned time period without any test article-related abnormalities and their health was considered within normal limits throughout the duration of the study. Animal body weight, as well as complete blood counts and serum chemistry values were within the expected ranges for the study.

3.2 Tissue Expander Filling

Tissue expander filling was completed successfully post implantation in all animals. In addition, tissue expanders did not deflate when covered by the support device, indicating that the support device does not affect tissue expander filling; nor does it lead to premature deflations of the expander.

3.3 Incision Site Evaluations

On sides implanted with the support device, one animal was noted as having mild incision redness. In contrast, on the control side, there were multiple animals with incision observations: incision site granulation, minor dehiscence, superficial dehiscence with granulation, and seroma.

3.4 Anatomic Pathology

Gross necropsy indicated the animals were in good health and there were no anomalies related to the test or control article. At 12 weeks post implantation, no gross traces of the support device remained.

3.5 Mechanical Testing

The ball burst testing conducted on explanted capsule tissue indicated the average wall stress and burst strength were comparable in the test (with support structure) and control capsules. Wall stress was lower than unimplanted matrix through the 12-week time point. However, burst strength increased through 12 weeks, approaching the strength of unimplanted matrix.

3.6 Histopathology

The histopathology assessment indicated there was a mild reaction post implantation and prior to full absorption, and minimal to no reaction at 12 weeks post implantation for both the support device wrapped tissue expander and control tissue expander (no support device). At 12 weeks, the support device was completely absorbed with no identifiable matrix fibers present. The histopathology of the capsule surrounding the implant concluded there to be minimal to no reaction at 12 weeks post implantation. Similar to the anatomic pathology findings, there were no pathologic changes indicative of toxic injury in the organs.

3.7 Tissue Expander Wear

Tissue expander wear was assessed and demonstrated there were no outlier features indicating wear.

The support device did not contribute observable features to the expander shell.

3.8 Conclusions from the GLP Study

The GLP study provides data to support the following: (1) the support device is fully absorbed by 12 weeks post implantation; (2) there is no adverse tissue response; (3) the support device does not provide resistance to tissue expansion post-implantation; (4) the support device does not lead to degradation of the tissue expander; and (5) plasma testing for systemic levels of Rifampin and Minocycline were below detection limits at all timepoints.

It should be understood that the disclosed embodiments are not representative of all claimed embodiments. As such, certain aspects of the disclosure have not been discussed herein. That alternate embodiments may not have been presented for a specific portion of the innovations or that further undescribed alternate embodiments may be available for a portion is not to be considered a disclaimer of those alternate embodiments. Thus, it is to be understood that other embodiments can be utilized, and functional, logical, operational, organizational, structural and/or topological modifications may be made without departing from the scope of the disclosure. As such, all examples and/or embodiments are deemed to be non-limiting throughout this disclosure Some embodiments described herein relate to methods. It should be understood that such methods can be computer implemented methods (e.g., instructions stored in memory and executed on processors). Where methods described above indicate certain events occurring in certain order, the ordering of certain events can be modified. Additionally, certain of the events can be performed repeatedly, concurrently in a parallel process when possible, as well as performed sequentially as described above. Furthermore, certain embodiments can omit one or more described events.

As used in this specification and/or any claims included herein the singular forms "a," "an," and "the" include plural referents unless the context clearly dictates otherwise. Thus, for example, the term "a member" is intended to mean a single member or a combination of members, "a material" is intended to mean one or more materials, and/or the like.

As used herein, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one implementation, to at least one, optionally including more than one, A, with no B present (and optionally including elements other than B); in another implementation, to at least one, optionally including more than one, B, with no A present (and optionally including elements other than A); in yet another implementation, to at least one, optionally including more than one, A, and at least one, optionally including more than one, B (and optionally including other elements); etc.

As used herein, the term "set" can refer to multiple features or a singular feature with multiple parts and/or components. For example, when referring to a set of light sources, the set of light sources can be considered as one single light source with multiple components (e.g., a lens, case reflective cavity, diode, etc.), or the set of light sources can be considered as multiple, distinct light sources.

As used herein, the terms "about," "approximately," and/or "substantially" when used in connection with stated value(s) and/or geometric structure(s) or relationship(s) is intended to convey that the value or characteristic so defined is nominally the value stated or characteristic described. In some instances, the terms "about," "approximately," and/or "substantially" can generally mean and/or can generally contemplate a value or characteristic stated within a desirable tolerance (e.g., plus or minus 10% of the value or characteristic stated). For example, a value of about 0.01 can include 0.009 and 0.011, a value of about 0.5 can include 0.45 and 0.55, a value of about 10 can include 9 to 11, and a value of about 1000 can include 900 to 1100. Similarly, a first surface may be described as being substantially parallel to a second surface when the surfaces are nominally parallel. While a value, structure, and/or relationship stated may be desirable, it should be understood that some variance may occur as a result of, for example, manufacturing tolerances or other practical considerations (such as, for example, the pressure or force applied through a portion of a device, conduit, lumen, etc.). Accordingly, the terms "about," "approximately," and/or "substantially" can be used herein to account for such tolerances and/or considerations.

The invention claimed is:

1. A kit, comprising:
 a matrix sheet including a polymer coating that includes one or more active pharmaceutical ingredients; and
 a foldable sheet including one or more templates, the one or more templates including at least one of:
  a partial support template configured for use in shaping the matrix sheet into a first support device configured to provide partial coverage for a breast prosthesis including a tissue expander or a breast implant; and a full support template configured for use in shaping the matrix sheet into a second support device configured to provide full coverage for a breast prosthesis, the foldable sheet configured to be folded into an envelope form that is configured to enclose around the matrix sheet to maintain the matrix sheet in a sterile environment therein.

2. The kit of claim 1, wherein the matrix sheet is bioabsorbable.

3. The kit of claim 1, wherein the matrix sheet includes at least one of polylactic acid (PLA), polyglycolic acid (PGA), poly(L-lactide), poly(D,L-lactide), poly(L-lactide-co-D,L-lactide), poly(L-lactide-co-glycolide), poly(D, L-lactide-co-glycolide), poly(glycolide-co-trimethylene carbonate), poly(D,L-lactide-co-caprolactone), poly(glycolide-co-caprolactone), polydioxanone (PDO), prolyl 4-hydroxylase subunit beta (P4HB), or polycaprolactone (PCL), copolymers, terpolymers and blends thereof.

4. The kit of claim 1, wherein the matrix sheet is a knitted or woven textile.

5. The kit of claim 4, wherein the matrix sheet includes at least one of weave, warp knits, or weft knits.

6. The kit of claim 1, wherein the matrix sheet is an acellular tissue matrix.

7. The kit of claim 1, wherein the polymer coating includes tyrosine-based polyarylate and includes an antibacterial agent.

8. The kit of claim 1, wherein the foldable sheet includes a first section that can be folded over a second section, the first section including the partial support template and the second section including the full support template.

9. The kit of claim 1, wherein the partial support template is a first partial support template, and the one or more templates further includes a second partial support template.

10. The kit of claim 9, wherein the second partial support template is smaller than the first partial support template.

11. The kit of claim 10, wherein the first partial support template includes the second partial support template, a border surrounding the second partial support template, and a set of perforations disposed between the border and the second partial support template, the first partial support template being convertible into the second partial support template by breaking the set of perforations to remove the border.

12. The kit of claim 10, wherein the foldable sheet includes a first section that can be folded over a second section, the first section including the first and second partial support templates and the second section including the full support template.

13. The kit of claim 1, wherein the partial support template has a crescent shape such that the first support device is configured to cover a lower pole of the breast prosthesis.

14. The kit of claim 1, wherein the full support template has a shape including a plurality of extensions such that the second support device includes a plurality of corresponding extensions each configured to wrap around the breast prosthesis and to be affixed to a posterior side of the breast prosthesis.

15. The kit of claim 1, wherein the foldable sheet further includes at least one slot and at least one tab configured to fit through a corresponding slot to hold the foldable sheet in the envelope form.

16. A kit, comprising:
at least one pre-shaped matrix material, the at least one pre-shaped matrix material including:

a central region configured to cover a central portion of an anterior side of a breast prosthesis, and a plurality of extensions extending from the central region, each of the plurality of extensions configured to wrap around a portion of the breast prosthesis, the plurality of extensions configured to be affixed to surrounding tissue to secure the breast prosthesis in place; and a foldable sheet configured to be folded into an envelope form that is configured to enclose around the at least one pre-shaped matrix material to maintain at least one pre-shaped matrix material in a sterile environment therein.

17. The kit of claim 16, wherein each extension from the plurality of extensions includes:

a first section configured to cover a portion of the anterior side of the breast prosthesis;

a second section extending from the first section and having a narrower width than the first section, the second section configured to wrap around a side of the breast prosthesis; and a third section extending from the second section and increasing to a greater width than the second section before tapering to an apex, the third section configured to cover at least a portion of a posterior side of the breast prosthesis.

18. The kit of claim 17, wherein the apex of each of the plurality of extensions is configured to be coupled to one another at a posterior side of the breast prosthesis to secure the at least one pre-shaped matrix material to the breast prosthesis.

19. The kit of claim 17, wherein a maximum width of the third section is smaller than a maximum width of the first section of each of the plurality of extensions.

20. The kit of claim 16, wherein the at least one pre-shaped matrix material is substantially inelastic when being positioned around the breast prosthesis.

21. The kit of claim 16, wherein the at least one pre-shaped matrix material includes a polymer coating that includes active pharmaceutical ingredients.

22. The kit of claim 16, wherein the plurality of extensions includes four extensions.

23. A kit, comprising:
a matrix sheet; and
a foldable sheet including one or more templates, the one or more templates including at least one of:

a partial support template configured for use in shaping the matrix sheet into a first support device configured to provide partial coverage for a breast prosthesis including a tissue expander or a breast implant; and a full support template configured for use in shaping the matrix sheet into a second support device configured to provide full coverage for a breast prosthesis, the foldable sheet configured to be folded into an envelope form that is configured to enclose around the matrix sheet to maintain the matrix sheet in a sterile environment therein, the foldable sheet including a first section that can be folded over a second section, the first section including the partial support template and the second section including the full support template.

24. The kit of claim 23, wherein the matrix sheet is bioabsorbable.

25. The kit of claim 23, wherein the matrix sheet includes at least one of polylactic acid (PLA), polyglycolic acid (PGA), poly(L-lactide), poly(D,L-lactide), poly(L-lactide-co-D,L-lactide), poly(L-lactide-co-glycolide), poly(D, L-lactide-co-glycolide), poly(glycolide-co-trimethylene carbonate), poly(D,L-lactide-co-caprolactone), poly(glycolide-co-caprolactone), polydioxanone (PDO), prolyl 4-hydroxylase subunit beta (P4HB), or polycaprolactone (PCL), copolymers, terpolymers and blends thereof.

26. The kit of claim 23, wherein the matrix sheet is an acellular tissue matrix.

27. A kit, comprising:
a matrix sheet including; and
a foldable sheet including one or more templates, the one or more templates including at least one of:
a first partial support template configured for use in shaping the matrix sheet into a first support device configured to provide partial coverage for a breast prosthesis including a tissue expander or a breast implant;
a second partial support template; and
a full support template configured for use in shaping the matrix sheet into a second support device configured to provide full coverage for a breast prosthesis,
the foldable sheet configured to be folded into an envelope form that is configured to enclose around the matrix sheet to maintain the matrix sheet in a sterile environment therein.

28. The kit of claim 27, wherein the second partial support template is smaller than the first partial support template.

29. The kit of claim 28, wherein the first partial support template includes the second partial support template, a border surrounding the second partial support template, and a set of perforations disposed between the border and the second partial support template,
the first partial support template being convertible into the second partial support template by breaking the set of perforations to remove the border.

30. The kit of claim 28, wherein the foldable sheet includes a first section that can be folded over a second section, the first section including the first and second partial support templates and the second section including the full support template.

31. A kit, comprising:
a matrix sheet; and
a foldable sheet including one or more templates, the one or more templates including at least one of:
a partial support template configured for use in shaping the matrix sheet into a first support device configured to provide partial coverage for a breast prosthesis including a tissue expander or a breast implant; and
a full support template configured for use in shaping the matrix sheet into a second support device configured to provide full coverage for a breast prosthesis, the full support template having a shape including a plurality of extensions such that the second support device includes a plurality of corresponding extensions each configured to wrap around the breast prosthesis and to be affixed to a posterior side of the breast prosthesis,
the foldable sheet configured to be folded into an envelope form that is configured to enclose around the matrix sheet to maintain the matrix sheet in a sterile environment therein.

32. The kit of claim 31, wherein the matrix sheet is bioabsorbable.

33. The kit of claim 31, wherein the matrix sheet includes at least one of polylactic acid (PLA), polyglycolic acid (PGA), poly(L-lactide), poly(D,L-lactide), poly(L-lactide-co-D,L-lactide), poly(L-lactide-co-glycolide), poly(D, L-lactide-co-glycolide), poly(glycolide-co-trimethylene carbonate), poly(D,L-lactide-co-caprolactone), poly(glycolide-co-caprolactone), polydioxanone (PDO), prolyl 4-hydroxylase subunit beta (P4HB), or polycaprolactone (PCL), copolymers, terpolymers and blends thereof.

34. The kit of claim 31, wherein the matrix sheet is an acellular tissue matrix.

35. The kit of claim 31, wherein the partial support template has a crescent shape such that the first support device is configured to cover a lower pole of the breast prosthesis.

36. A kit, comprising:
a matrix sheet; and
a foldable sheet including one or more templates, the one or more templates including at least one of:
a partial support template configured for use in shaping the matrix sheet into a first support device configured to provide partial coverage for a breast prosthesis including a tissue expander or a breast implant; and
a full support template configured for use in shaping the matrix sheet into a second support device configured to provide full coverage for a breast prosthesis,
the foldable sheet configured to be folded into an envelope form that is configured to enclose around the matrix sheet to maintain the matrix sheet in a sterile environment therein, the foldable sheet including at least one slot and at least one tab configured to fit through a corresponding slot to hold the foldable sheet in the envelope form.

37. The kit of claim 36, wherein the matrix sheet is bioabsorbable.

38. The kit of claim 36, wherein the matrix sheet includes at least one of polylactic acid (PLA), polyglycolic acid (PGA), poly(L-lactide), poly(D,L-lactide), poly(L-lactide-co-D,L-lactide), poly(L-lactide-co-glycolide), poly(D, L-lactide-co-glycolide), poly(glycolide-co-trimethylene carbonate), poly(D,L-lactide-co-caprolactone), poly(glycolide-co-caprolactone), polydioxanone (PDO), prolyl 4-hydroxylase subunit beta (P4HB), or polycaprolactone (PCL), copolymers, terpolymers and blends thereof.

39. The kit of claim 36, wherein the matrix sheet is an acellular tissue matrix.

* * * * *